United States Patent [19]

Kott et al.

[11] Patent Number: 5,635,104
[45] Date of Patent: *Jun. 3, 1997

[54] BLEACHING SOLUTIONS AND METHOD UTILIZING SELECTED BLEACH ACTIVATORS EFFECTIVE AT LOW PERHYDROXYL CONCENTRATIONS

[75] Inventors: Kevin L. Kott; Alan D. Willey, both of Cincinnati; Gregory S. Miracle, Forest Park; James C. T. R. Burckett-St. Laurent, Cincinnati, all of Ohio

[73] Assignee: The Procter & Gamble Company, Cincinnati, Ohio

[*] Notice: The term of this patent shall not extend beyond the expiration date of Pat. No. 5,405,413.

[21] Appl. No.: 341,807

[22] Filed: Nov. 18, 1994

Related U.S. Application Data

[63] Continuation-in-part of Ser. No. 82,207, Jun. 24, 1993, Pat. No. 5,405,413.

[51] Int. Cl.$^6$ .............................. C01B 11/00; C01B 7/00; C11D 3/02
[52] U.S. Cl. .................... 252/186.1; 252/186.2; 252/186.31; 252/186.38; 252/186.39; 510/220; 510/276
[58] Field of Search ............... 352/186.1, 186.2, 352/186.31, 186.38, 187.2; 510/220, 276

[56] References Cited

U.S. PATENT DOCUMENTS

| | | | |
|---|---|---|---|
| 3,042,621 | 7/1962 | Kirschenbauer | 252/99 |
| 3,075,921 | 1/1963 | Brocklehurst | 252/99 |
| 3,177,148 | 4/1965 | Bright | 252/99 |
| 3,637,339 | 1/1972 | Gray | 8/111 |
| 3,775,332 | 11/1973 | Heins | 252/95 |
| 3,812,247 | 5/1974 | Heins | 424/62 |
| 4,013,575 | 3/1977 | Castrantas | 252/104 |
| 4,545,784 | 10/1985 | Sanderson | 8/107 |
| 4,778,618 | 10/1988 | Fong | 252/186.23 |
| 4,790,952 | 12/1988 | Steichen | 252/186.39 |
| 4,820,437 | 4/1989 | Akabane et al. | 252/186.39 |
| 5,405,412 | 4/1995 | Willey | 8/111 |
| 5,405,413 | 4/1995 | Willey | 8/111 |
| 5,460,747 | 10/1995 | Gosselink et al. | 252/186.38 |
| 5,500,153 | 3/1996 | Figueroa et al. | 252/174 |

FOREIGN PATENT DOCUMENTS

| | | | |
|---|---|---|---|
| 257700 | 3/1988 | European Pat. Off. | C11D 3/39 |
| 677576 | 10/1995 | European Pat. Off. | C11D 3/39 |
| 02115154 | 4/1990 | Japan | C07C 23/52 |
| WO93/12067 | 6/1993 | WIPO | C07C 69/66 |
| WO93/20167 | 10/1993 | WIPO | C09K 3/00 |
| WO94/18299 | 8/1994 | WIPO | C11D 3/39 |
| WO94/18298 | 8/1994 | WIPO | C11D 3/39 |
| WO94/27970 | 12/1994 | WIPO | C07D 223/10 |

OTHER PUBLICATIONS

Aikawa CA 85:1086z, 1976.
Stehlicek CA 108:187402w, 1988.
Ishida CA 88:169981y, 1978.
Kirk Othmer, Encyclopedia of Chemical Technology, vol. 7, 4th Ed., 1993, pp. 1072–1117.
Kirk Othmer, Encyclopedia of Chemical Technology, vol. 9, 4th Ed., 1993, pp. 567–620.
Kirk Othmer, Encyclopedia of Chemical Technology, vol. 4, 4th Ed., 1994, pp. 271–299.

*Primary Examiner*—Shean C. Wu
*Attorney, Agent, or Firm*—Michael D. Jones; Brian M. Bolam; Kim W. Zerby

[57] ABSTRACT

Improved aqueous bleaching solutions formed by reacting a bleach activator having a perhydrolysis selectivity coefficient of 5 or greater and a low-pH perhydrolysis-efficiency coefficient of 0.15 or higher are provided. More specifically, the invention relates to bleaching solutions which provide enhanced cleaning/bleaching benefits though the selection of bleach activators at mildly alkaline washing solutions or in the presence of reduced-levels of hydrogen peroxide.

28 Claims, No Drawings

BLEACHING SOLUTIONS AND METHOD UTILIZING SELECTED BLEACH ACTIVATORS EFFECTIVE AT LOW PERHYDROXYL CONCENTRATIONS

This application is a continuation-in-part of U.S. Ser. No. 08/082,207, filed Jun. 24, 1993, now U.S. Pat. No. 5,405,413 issuing Apr. 11, 1995.

FIELD OF THE INVENTION

The present invention relates to improved aqueous bleaching solutions. The improvement hinges on the identification of particular bleach activators which enhance or boost the performance of bleaching agents such as perborate. The bleaching solutions are useful in fabric laundering and bleaching, automatic dishwashing, hard surface cleaning, cleaning involving use of bleach additives, and the like.

BACKGROUND OF THE INVENTION

Hydrogen peroxide bleaching under conditions in which concentrations of $H_2O_2$ and alkali are low is a considerable challenge to the laundry detergent industry. Similar challenges are also faced by the formulator of automatic dishwashing detergent compositions (ADD's), which are expected to efficiently cleanse and sanitize dishware, often under heavy soil loads, typically involving mildly acidic food residues. The problems associated with the formulation of truly effective cleaning and bleaching systems have been exacerbated by legislation which limits the use of effective ingredients such as phosphate builders in many regions of the world.

Domestic bleaching systems for fabrics and hard surfaces can be simple, such as alkaline hypochlorite, but such systems are frequently potentially aggressive. More complex systems have evolved, centering on the use of a hydrogen peroxide source. Such systems can further involve mixtures of various detersive surfactants to remove a wide variety of soils and stains from surfaces. In addition, various detersive enzymes, soil suspending agents, non-phosphorus builders, optical brighteners, and the like may be added to boost overall cleaning performance. Many fully-formulated cleaning compositions having a bleaching action contain oxygen bleach, which can be a perborate or percarbonate compound. While quite effective at high temperatures, perborates and percarbonates lose much of their bleaching function at the low to moderate temperatures increasingly favored in consumer product use. Accordingly, various bleach activators such as tetraacetylethylenediamine (TAED) and nonanoyloxy-benzenesulfonate (NOBS) have been developed to potentiate the bleaching action of perborate and percarbonate across a wide temperature range. NOBS is particularly effective on "dingy" fabrics.

A limitation with activators such as the widely commercialized TAED is that the wash solution or liquor should have a pH of about 10 or higher for best results. Since soils, especially from foods, are often acidic, detergent products are frequently quite alkaline or are buffered sufficiently to maintain a high pH so the bleach activator system can operate effectively throughout the wash. However, this need runs counter to providing milder formulations which could be improved in their compatibility with fabrics, glassware and/or skin. In cleaning operations below pH 10, many of the existing bleach activators lose their effectiveness or undergo competing side reactions which produce ineffective byproducts.

The search, therefore, continues for more effective activator materials, especially for use in mildly alkaline washing liquors or with decreased levels of perborate or other sources of hydrogen peroxide. Improved activator materials should be safe, effective, and will preferably be designed to interact with troublesome soils and stains. Various activators have been described in the literature. Many are esoteric and expensive.

It has now been determined that certain selected bleach activators are unexpectedly effective in removing soils and stains from fabrics and hard surfaces such as dishes even under low alkaline wash conditions or with decreased levels of hydrogen peroxide. These activators also have advantageously high ratios of rates of perhydrolysis to hydrolysis and of perhydrolysis to diacylperoxide formation. Without being limited by theory, these unusual rate ratios lead to a number of significant benefits for the instant activators, including increased efficiency, avoidance of wasteful byproduct formation in the wash, increased color compatibility, increased enzyme compatibility, and better stability on storage.

When selected and used as described herein, bleaching solutions are provided using the selected bleach activators to remove soils and stains not only from fabrics, but also from dishware in automatic dishwashing compositions, from kitchen and bathroom hard surfaces, and the like, with excellent results. The bleaching solutions are designed to function well over a wide range of washing or soaking temperatures and are compatible with rubber surfaces, such as those of sump hoses often used in European front-loading washing machines. Moreover, novel methods for producing such bleaching solutions are provided. In short, the compositions and methods herein provide a substantial advance over those known in the art, as will be seen from the disclosures hereinafter.

BACKGROUND ART

Bleach activators of various types are described in U.S. Pat. Nos. 4,545,784; 4,013,575; 3,075,921; 3,637,339; 3,177,148; 3,042,621; 3,812,247; 3,775,332; 4,778,618; 4,790,952; EP 257,700; WO 94/18299; WO 94/18298; WO 93/20167; WO 93/12067; and in JP 02115154. Other references include Aikawa CA 85:1086z; Stehlicek CA 108:187402w; Ishida CA 88:169981y; Kirk Othmer, Encyclopedia of Chemical Technology, Vol. 7, 4th Ed., 1993, pp. 1072–1117; Kirk Othmer, Encyclopedia of Chemical Technology, Vol. 4, 4th Ed., 1994, pp. 271–299; Kirk Othmer, Encyclopedia of Chemical Technology, Vol. 9, 4th Ed., 1993, pp. 567–620.

SUMMARY OF THE INVENTION

The present invention relates to bleaching solutions formed by reacting, under aqueous conditions, effective amounts of (a) a particularly selected bleach activator, specifically, one having a perhydrolysis selectivity coefficient, $K_P/K_D$, as defined hereinafter, of 5 or greater and a low-pH perhydrolysis-efficiency coefficient of 0.15 or higher, preferably, one forming at most one mole equivalent of a peracid per mole of bleach activator when perhydrolyzed; with (b) an effective amount of an oxygen bleach source.

Preferred bleaching solutions are aqueous and are directed to use in the home. Thus, they are generally substantially free from organic dry-cleaning solvents or similar substances having low suitability for home use.

Typical bleaching solutions herein are those formed by adding a bleach additive composition comprising said bleach activator to an aqueous alkaline cleaning bath comprising the oxygen bleach source.

Suitable bleaching solutions can be formed by the steps, in sequence, of: (i) mixing with water a granular or tablet-form detergent comprising both said bleach activator and said oxygen bleach source; and (ii) the above-identified reaction step.

Bleach activators for use herein have a low pH perhydrolysis efficiency coefficient of at least about 0.15, preferably at least about 0.30, more preferably at least about 0.5.

Bleaching solutions within the scope of the invention can suitably make use of an oxygen bleach source selected from the group consisting of hydrogen peroxide, perborate salts, percarbonate salts, peroxymonosulfate salts, and peroxydisulfate salts; mixtures can in general be used.

In preferred embodiments, bleaching solutions can be made using oxygen bleach source selected from the group consisting of perborate salts, percarbonate salts and mixtures thereof. The bleach activator is preferably selected from the group consisting of:
p-nitrobenzoyl caprolactam; p-nitrobenzoylvalerolactam; linear or branched $C_2$–$C_9$ alkylsulfonylbenzoylcaprolactam; linear or branched $C_2$–$C_9$ alkylsulfonylbenzoylvalerolactam; linear or branched $C_2$–$C_9$ alkyloxysulfonylbenzoylcaprolactam; linear or branched $C_2$–$C_9$ alkyloxysulfonyl-benzoylvalerolactam; linear or branched $C_2$–$C_9$ alkyl(amino)sulfonylbenzoylcaprolactam; linear or branched $C_2$–$C_9$ alkyl(amino)sulfonylbenzoylvalerolactam; 2-furoylcaprolactam; 2-furoylvalerolactam; 3-furoylcaprolactam; 3-furoylvalerolactam; 5-nitro-2-furoyl-caprolactam; 5-nitro-2-furoylvalerolactam; 1-naphthylcaprolactam; 1-naphthylvalerolactam; and mixtures thereof. More preferably in these embodiments, the bleach activator is selected from the group consisting of linear or branched $C_2$–$C_9$ alkylsulfonylbenzoylcaprolactam; linear or branched $C2$–$C_9$ alkylsulfonylbenzoylvalerolactam; linear or branched $C_2$–$C_9$ alkyloxysulfonylbenzoylcaprolactam; linear or branched $C_2$–$C_9$ alkyloxysulfonylbenzoylvalerolactam; linear or branched $C_2$–$C_9$ alkyl(amino)sulfonylbenzoylcaprolactam; linear or branched $C_2$–$C_9$ alkyl(amino)sulfonylbenzoylvalerolactam; 2-furoylcaprolactam; 2-furoylvalerolactam; 3-furoylcaprolactam; 3-furoylvalerolactam; 5-nitro-2-furoylcaprolactam; 5-nitro-2-furoyl-valerolactam; and mixtures thereof.

Remarkably, the bleaching solutions can be made even when the initial level of said oxygen bleach source is low, for example an initial concentration of oxygen bleach source being in the range from about $10^{-4}$ to about $10^{-10}$ moles per mole of said bleach activator. Note that "initial" is used to indicate "as rapidly as can be measured using conventional analytical methodology" that oxygen bleach is consumed during bleaching and its concentration may vary during cleaning or laundering operations. Since differed hydrogen peroxide sources can vary in their content of hydrogen peroxide, concentrations of oxygen bleach source herein are expressed as perhydroxyl ion concentrations as measured at a pH of about 7.5.

Preferred bleaching solutions can be provided under other normally adverse circumstances or composition regimes, for example wherein the pH of said bleaching solution, as formed, is from about 6.5 to about 9.5, preferably from about 7 to about 9, more preferably from about 7.5 to about 8.5.

These pH ranges span conditions under which perhydroxyl concentrations are normally low at affordable levels of oxygen bleach sources (typically about 25% or less oxygen bleach in a granular bleaching detergent) since hydrogen peroxide is then well removed from its pKa (above 11). Under these conditions, perhydrolysis is normally both inefficient and ineffective.

In typical embodiments herein, bleaching solutions can include the selected bleach activator at initial levels of from about 1 to about 1000 ppm, more typically from about 1 to about 300 ppm, of the bleaching solution.

In view of the remarkable improvement in bleaching on account of the use of the selected bleach activators, preferred bleaching solutions herein can have a low soil level resistivity.

Soil Level Resistivity

It is well known by those skilled in the art that many soils typically encountered in detergent applications are effectively acidic in nature. As such, the type and amount of soil encountered may significantly lower the in-use pH of a bleaching solution. Common body soils, for example, can include sebacious fatty acids, citric acid, lactic acid and the like as well as triglyceride esters which can hydrolyze in an alkaline aqueous environment to produce additional carboxylic acid species. The response of a bleaching solution to the introduction of acidic components can be gauged by measuring the change in pH of said solution upon addition of a model acid, acetic acid.

The "Soil Level Resistivity" (SLR) of a bleaching solution is determined as follows: A 1 kg sample of the bleaching solution is stirred for 30 minutes and the pH measured immediately thereafter. The measured pH is defined as $pH_i$. After determining $pH_i$, 30 ml of an acetic acid solution (prepared by diluting 1 ml of glacial acetic acid with distilled, deionized water to a total volume of 1000 ml) is added to said bleaching solution and the resulting mixture is stirred for 5 minutes, after which a second pH ($pH_f$) is measured.

The soil level resistivity, denoted as $\sigma$ is defined by the equation $$\sigma = 10 \times (\theta/\Gamma);$$

where $$\Gamma = pH_i - pH_f,$$

$$\theta = \delta^2/pH_i,$$

and wherein, when $pH_i \geq pH_c$, $$\delta = pH_i - pH_c,$$

and when $pH_i < pH_c$, $\delta = 0$. Said $pH_c$ is the critical pH, given by $$pH_c = pK_{\alpha_{peracid}} + \Delta pK_c$$

where $\Delta pK_c$ is the critical $\Delta pK$ given by $$\Delta pK_c = 100[1/pK_{\alpha_{peracid}} - (1/pH_{pref})]$$

wherein $pK_{\alpha_{peracid}}$ is the aqueous $pK_{60}$ of the peracid species present in the standard solution, and $pH_{pref}$ is the preferred pH, set equal to the midpoint of the most preferred in-use wash pH range of 7.5–8.5. When two or more peracid species are present, the lowest $pK_{\alpha_{peracid}}$ value is used to calculate $\delta$.

The soil level resistivity of any particular detergent formulation can be designated based on its $\sigma$ value as shown in the table below.

| SLR Designation | σ Value |
| --- | --- |
| high | σ > 25 |
| moderate | 10 < σ ≦ 25 |
| low | σ ≦ 10 |

Other preferred bleaching solutions herein are substantially free from phosphate builders such as sodium tripolyphosphate and can also desirably be boron- free. The instant bleaching solutions can moreover be substantially free from chlorine bleach.

The invention further encompasses bleaching solutions prepared by mixing a bleach additive which is substantially free from oxygen bleach source with an aqueous bath formed by mixing with water a conventional detergent product containing a hydrogen peroxide source such as sodium perborate, sodium percarbonate, or the like.

In the method embodiments, the development encompasses a method for forming a bleaching solution comprising a step of reacting, under aqueous conditions, effective amounts of (a) a bleach activator having a perhydrolysis selectivity coefficient of 5 or greater and a low-pH perhydrolysis-efficiency coefficient of 0.15 or higher; with (b) an effective amount of an oxygen bleach source.

In a preferred method, said bleach activator forms at most one mole equivalent of a peracid per mole of bleach activator when perhydrolyzed.

Other preferred methods include a method further comprising a preceding step of adding a bleach additive composition comprising said bleach activator to an aqueous alkaline cleaning bath comprising said oxygen bleach source in dissolved form; a method for bleaching fabrics comprising any of the earlier-defined methods followed by a step comprising treating fabrics with said bleaching solution; a method wherein the first reaction step is a supplementary step in an otherwise conventional method for washing dishware in a domestic automatic dishwashing appliance (preferably said step is further characterized in that it a post-mainwash step in which said oxygen bleach source consists essentially of rinse-cycle carryover); and a method further comprising a preceding step of dissolving a granular or tablet-form detergent comprising both said bleach activator and said oxygen bleach source.

In the methods herein, said low pH perhydrolysis efficiency coefficient is at least about 0.15. The oxygen bleach source as employed in the method can suitably be selected from the group consisting of hydrogen peroxide, perborate salts, percarbonate salts, peroxymonosulfate salts, and peroxydisulfate salts.

In other preferred methods said bleach activator has an aqueous solubility at 25° C. of about 10 ppm or higher.

In a highly preferred method, said oxygen bleach source is selected from the group consisting of perborate salts, percarbonate salts and mixtures thereof and wherein said bleach activator is selected from the group consisting of: p-nitrobenzoyl caprolactam; p-nitrobenzoylvalerolactam; linear or branched C2–C9 alkyl-sulfonylbenzoylcaprolactam; linear or branched C2–C9 alkylsulfonylbenzoylvalerolactam; linear or branched C2–C9 alkyloxysulfonylbenzoylcaprolactam; linear or branched C2–C9 alkyloxysulfonylbenzoylvalerolactam; linear or branched C2–C9 alkyl(amino)sulfonyl-benzoylcaprolactam; linear or branched C2–C9 alkyl(amino)sulfonylbenzoylvalerolactam; linear or branched C2–C9 alkylsulfonylnaphthylcaprolactam; linear or branched C2–C9 alkylsulfonylnaphthylvalerolactam; linear or branched C2–C9 alkyloxysulfonylnaphthyl-caprolactam; linear or branched C2–C9 alkyloxysulfonylnaphthyl-valerolactam; linear or branched C2–C9 alkyl(amino) sulfonylnaphthyl-caprolactam; linear or branched C2–C9 alkyl(amino) sulfonylnaphthylvalerolactam; 2-furoylcaprolactam; 2-furoylvalerolactam; 3-furoyl-caprolactam; 3-furoylvalerolactam; 5-nitro-2-furoylcaprolactam; 5-nitro-2-furoyl-valerolactam; 1-naphthylcaprolactam; 1-naphthylvalerolactam; and mixtures thereof. Moreover the initial level of said oxygen bleach source in said bleaching solution upon formation is from about $10^{-4}$ to about $10^{-10}$ moles per mole of said bleach activator. The pH of said bleaching solution, as formed, is from about 7 to about 8.5, and the activator is at an initial level of from about 1 to about 300 ppm of said bleaching solution. The bleach additive is substantially free from oxygen bleach source.

By "effective amount" herein is meant an amount which is sufficient, under whatever comparative test conditions are employed, to enhance cleaning of a soiled surface. Likewise, the term "catalytically effective amount" refers to an amount which is sufficient under whatever comparative test conditions are employed, to enhance cleaning of a soiled surface.

All percentages, ratios and proportions herein are by weight, unless otherwise specified. All documents cited are, in relevant part, incorporated herein by reference.

DETAILED DESCRIPTION OF THE INVENTION

The present invention relates to bleaching solutions for the domestic treatment of fabrics or hard surfaces and to methods for their formation and use. The bleaching solutions are formed from compositions which comprise a selected bleach activator, preferably accompanied by a source of hydrogen peroxide, and also include embodiments which are made by combining bleach additives substantially free from hydrogen peroxide or hydrogen peroxide releasing sources with wash baths comprising such sources, optionally but preferably with additional components, such as surfactants, bleach catalysts, and the like.

The bleaching solutions herein comprise an effective amount of one or more performance-enhanced bleach activators. These activators are selected to have particular properties so that they are more effective in promoting bleaching under certain use conditions in which TAED or similar conventional bleach activators are relatively inefficient and ineffective.

In general, suitable activators for the present bleaching solutions comprise one or more moieties RC(O)— which produce a peracid RC(O)—OOH on perhydrolysis (reaction with perhydroxyl, ⁻OOH). R is selected such that the difference in aqueous $pK_a$ between acetic acid and the carboxylic acid analog, RC(O)OH, of said peracid is at least 0.6, preferably at least about 1.2. When it is stated that the difference in aqueous $pK_a$ between acetic acid and the carboxylic acid analog, RC(O)OH, of a peracid is at least 0.6, the following subtraction, in the indicated order, is made: $pK_a$ (CH$_3$C(O)OH)—$pK_a$(RC(O)OH).

These performance-enhanced bleach activators also have a low pH perhydrolysis efficiency coefficient (a practical measure of peracid formation further defined hereinafter) of at least about 0.15, preferably at least about 0.3, and a ratio $kp/k_D \geq 5$, more preferably $kp/k_D \geq 30$, still more preferably $kp/k_D \geq 50$, wherein kp is the rate constant for perhydrolysis of the performance-enhanced bleach activator and $k_D$ is the rate constant for the formation of a diacylperoxide, RC(O)OOC(O)R, from the performance-enhanced bleach activator.

The activators useful herein preferably comprise one or me e moieties, L, which act as leaving groups on perhydrolysis. Thus, preferred performance enhanced bleach activators herein have the formula RC(O)—L.

Preferred leaving groups, L, comprise at least one tricoordinate nitrogen atom covalently connecting L to RC(O)—. Furthermore, the preferred performance-enhanced bleach activators are capable of forming a maximum of one mole equivalent of said peracid on perhydrolysis and have $k_H \leq 10M^{-1} s^{-1}$ and a ratio $kp/k_H \geq 1$, more preferably $kp/k_H \geq 2$, wherein $k_H$ is the rate constant for hydrolysis of the performance-enhanced bleach activator and kp is said rate constant for perhydrolysis.

In general, R and L can independently be neutral or can be charged either positively or negatively. In preferred compositions, both R and L are neutral wherein L is typically selected from suitably substituted or unsubstituted lactams, 2-alkyl 4,5-dihydroimidazoles, and mixtures thereof, and R is illustrated by p-nitrophenyl or, more preferably, an alkylsulfonylphenyl moiety. Suitable R moieties are illustrated at length hereinafter.

In preferred embodiments, R can be connected to —C(O)— through a carbon atom which forms part of an aromatic ring, and L can be selected such that its conjugate acid, HL, has an aqueous $pK_a$ in the range from greater than about 13 to less than about 17.

In other highly preferred embodiments, the performance-enhanced bleach activator as a whole, or simply its leaving group, L, is free from any heterocyclic moiety wherein a hydrogen atom is attached to a carbon atom that is alpha to both a carbonyl group and a multivalent heteroatom.

Compositions useful in this invention may include additional detergent additives including one or more of the following ingredients: surfactants, low-foaming automatic dishwashing surfactants, ethoxylated nonionic surfactants, bleach stable thickeners, transition-metal chelants, builders, flourescent whitening agents, and buffering agents. The compositions are typically formulated below drycleaning-useful levels of any organic solvent. Preferably the compositions are substantially free from organic solvents. Preferred builders are selected from the group consisting of citrate, layered silicate, zeolite A, zeolite P and mixtures thereof.

A typical bleach-additive composition useful herein comprises:

(a) from about 0.1% to about 30% of said performance-enhanced bleach activator;
(b) from about 0.1% to about 60% of nonionic surfactant; and
(c) from about 0.001% to about 10% of a transition-metal chelant.

A typical bleaching composition useful herein comprises:

(a) from about 0.1% to about 30% of said performance-enhanced bleach activator;
(b) from about 0.1% to about 70% of a hydrogen peroxide source; and
(c) from about 0.001% to about 10% of a transition-metal chelant.

In preferred embodiments, the bleaching compositions deliver an aqueous pH in the range from about 6.5 to about 9.5, more preferably from about 7 to about 9, still more preferably from about 7.5 to about 8.5, and the level of source of hydrogen peroxide is sufficient to provide a perhydroxyl ion concentration, as measured at a pH of about 7.5, of about $10^{-4}$ to about $10^{-10}$ molar, more preferably about $10^{-5}$ to about $10^{-8}$ molar.

Additional illustrations of the bleach-additive or bleaching compositions which are useful in the bleaching solutions herein are those comprising from about 0.1% to about 10% of a performance-enhanced bleach activator selected from the group consisting of:

p-nitrobenzoyl caprolactam; p-nitrobenzoylvalerolactam; linear or branched $C_2$-$C_9$ alkylsulfonylbenzoylcaprolactam; linear or branched $C_2$-$C_9$ alkylsulfonylbenzoylvalerolactam; linear or branched $C_2$-$C_9$ alkyloxysulfonylbenzoylcaprolactam; linear or branched $C_2$-$C_9$ alkyloxysulfonylbenzoylvalerolactam; linear or branched $C_2$-$C_9$ alkyl(amino)sulfonyl-benzoylcaprolactam; linear or branched $C_2$-$C_9$ alkyl(amino)sulfonylbenzoylvalerolactam; 2-furoylcaprolactam; 2-furoylvalerolactam; 3-furoylcaprolactam; 3-furoylvalerolactam; 5-nitro-2-furoylcaprolactam; 5-nitro-2-furoylvalerolactam; 1-naphthylcaprolactam; 1-naphthylvalero-lactam; and mixtures thereof. More preferably in these embodiments, the performance-enhanced bleach activator is selected from the group consisting of linear or branched $C_2$-$C_9$ alkylsulfonylbenzoylcaprolactam; linear or branched $C_2$-$C_9$ alkylsulfonylbenzoylvalerolactam; linear or branched $C_2$-$C_9$ alkyloxysulfonylbenzoylcaprolactam; linear or branched $C_2$-$C_9$ alkyloxysulfonylbenzoylvalerolactam; linear or branched $C_2$-$C_9$ alkyl(amino)sulfonylbenzoylcaprolactam; linear or branched $C_2$-$C_9$ alkyl(amino)sulfonylbenzoylvalerolactam; 2-furoylcaprolactam; 2-furoylvalerolactam; 3-furoylcaprolactam; 3-furoylvalerolactam; 5-nitro-2-furoylcaprolactam; 5-nitro-2-furoylvalerolactam; and mixtures thereof.

In highly preferred embodiments, these compositions further comprise a bleach catalyst at the art-disclosed levels. bleaching solutions comprising such compositions have particularly significant bleaching performance enhancement as compared with otherwise identical solutions in which a conventional bleach activator such as TAED is used in place of the performance-enhanced bleach activator.

Additional performance-enhanced bleach activators include those compounds having the formula RC(O)—L, wherein L is selected from the group consisting of lactams and 4,5-dihydroimidazoles; R is selected from the group consisting of substituted phenyl having more than one chloro, bromo or nitro substituent; furan or substituted furan having one or more chloro, bromo, nitro, alkylsulfonyl or arylalkylsulfonyl substituents; 1-naphthyl; substituted 1-naphthyl; or substituted 2-naphthyl having one or more chloro, bromo or nitro substituents;

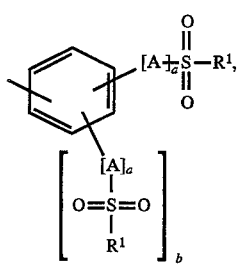

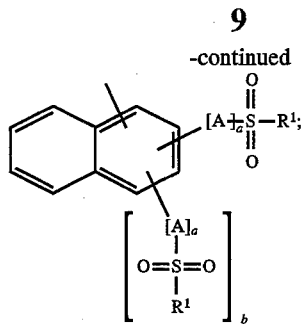

and mixtures thereof;

wherein in each structure a is independently 0 or 1, b is 0 or 1, and A is selected from O and $NR^2$ wherein $R^2$ is H or methyl; and wherein when a is 1 and A is O, $R^1$ is selected from alkyl, arylalkyl, alkoxy, aryloxy, alkylamino, and arylamino; when a is 1 and A is other than O, $R^1$ is selected from alkyl and arylalkyl.

The bleaching solutions herein, in general, comprise a source of bleach, typically a source of hydrogen peroxide, in addition to the activator component. Bleach additive compositions, however, may or may not have a hydrogen peroxide source built into the formulation. Whereas additive compositions are generally used in conjunction with conventional bleach-containing detergents, especially those formulated with sodium perborate or percarbonate, bleaching compositions according to the invention are typically used as "stand-alone" formulations delivering a full range of cleaning and bleaching effects.

As noted, preferred performance-enhanced bleach activators herein comprise one or more RC(O)— and —L moieties. In general, more than one of each of these can be present. Preferably, one of each is present, and they are covalently connected.

Moieties RC(O)

In preferred bleach activators useful herein, R is nonlimitingly illustrated by electronegatively substituted phenyl selected from the group consisting of p-chlorophenyl, m-chlorophenyl, p-nitrophenyl, 3,5-dichlorophenyl, and 3,5-dinitrophenyl, and mixtures thereof. In yet other preferred embodiments, R is selected from alkylsulfonylphenyl, arylalkylsulfonylphenyl, alkylsulfonyl naphthyl, arylalkylsulfonyl-naphthyl, and mixtures thereof. Note that when naphthyl is selected, unsubstituted 1-naphthyl or substituted 1- or 2-naphthyl is preferred. Other examples of preferred bleach activators include those wherein R is a substituted or unsubstituted furan, and wherein R is substantially free from chloro- or nitro- substituents.

Leaving Groups

The L moieties in the performance-enhanced bleach activators useful in this invention are preferably selected from the group consisting of unsubstituted lactams, substituted lactams, substituted or unsubstituted 2-alkyl 4,5-dihydroimidazoles, and mixtures thereof. Particularly preferred examples of L are those selected from the group consisting of:

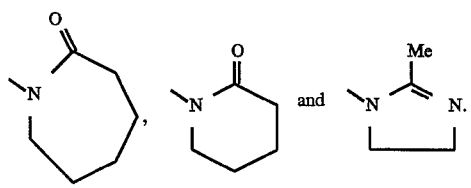

Performance Enhanced Bleach Activator Compounds

—In preferred performance—enhanced bleach activator compounds useful in the bleaching solutions of this invention, L is as indicated supra and R is selected from the group consisting of:

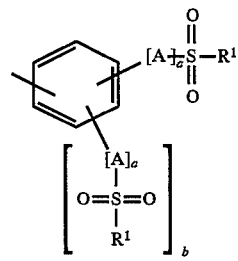

wherein a is independently 0 or 1, b is 0 or 1, A is selected from O and $NR^2$ wherein $R^2$ is H or methyl; when a is 0 or when a is 1 and A is O, $R^1$ is selected from alkyl, arylalkyl, alkoxy, aryloxy, alkylamino, and arylamino; when a is 1 and A is other than O, $R^1$ is selected from alkyl and arylalkyl; and (II) furan or substituted furan, having the formula:

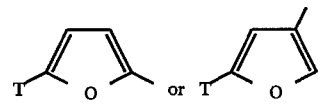

wherein T is selected from the group consisting of H, $NO_2$, Br, alkyl, and arylalkyl.

In a highly preferred embodiment of the performance boosting bleach activator, L is preferably selected from the group consisting of:

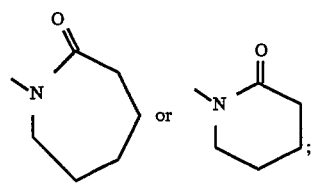

and R is selected from the group consisting of:

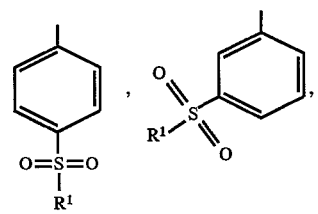

-continued

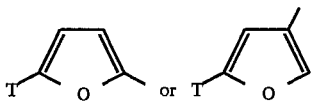

wherein $R^1$ is selected from alkyl, arylalkyl, alkoxy, aryloxy, alkylamino, and arylamino; and T is selected from the group consisting of H, Br, and $NO_2$. Compositions comprising these novel compounds are also included in the scope of this invention.

$pK_a$, Rate and Perhydrolysis Criticalities

In accordance with the present invention, there are provided bleaching compositions wherein the bleach activators are required to respect criticalities of $pK_a$ and criticalities relating to rates of perhydrolysis, hydrolysis and diacylperoxide formation. Furthermore, perhydrolysis effciency is important in selecting the bleach activator. All of these criticalities will be better understood and appreciated in light of the following disclosure.

$pK_a$ Value

The acids in which organic chemists have traditionally been interested span a range, from the weakest acids to the strongest, of about 60 pK units. Because no single solvent is suitable over such a wide range, establishment of comprehensive scales of acidity necessitates the use of several different solvents. Ideally, one might hope to construct a universal acidity scale by relating results obtained in different solvent systems to each other. Primarily because solute-solvent interactions affect acid-base equilibria diffently in different solvents, it has not proven possible to establish such a scale.

Water is taken as the standard solvent for establishing an acidity scale. It is convenient, has a high dielectric constant, and is effective at solvating ions. Equilibrium acidities of a host of compounds (e.g., carboxylic acids and phenols) have been determined in water. Compilations of pK data may be found in Perrin, D. D. "Dissociation Constants of Organic Bases in Aqueous Solution"; Butterworths: London, 1965 and Supplement, 1973; Serjeant, E. P.; Dempsey, B. "Ionisation Constants of Organic Acids in Aqueous Solution"; 2nd ed., Pergammon Press: Oxford, 1979. Experimental methods for determining $pK_a$ values are described in the original papers. The $pK_a$ values that fall between 2 and 10 can be used with a great deal of confidence; however, the further removed values are from this range, the greater the degree of skepticism with which they must be viewed.

For acids too strong to be investigated in water solution, more acidic media such as acetic acid or mixtures of water with perchloric or sulfuric acid are commonly employed; for acids too weak to be examined in water, solvents such as liquid ammonia, cyclohexylamine and dimethylsulfoxide have been used. The Hammett $H_o$ acidity function has allowed the aqueous acidity scale, which has a practical $pK_a$ range of about 0–12, to be extended into the region of negative $pK_a$ values by about the same range. The use of H_acidity functions that employ strong bases and cosolvents has similarly extended the range upward by about 12 $pK_a$ units.

The invention involves the use of leaving groups the conjugate acids of which are considered to be weak; they possess aqueous $pK_a$ values greater than about 13. To establish only that a given compound has an aqueous $pK_a$ above about 13 is straightforward. As noted above, values much above this are difficult to measure with confidence without resorting to the use of an acidity function. The measurement of the acidity of weak acids using the H_method, which has the advantage of an aqueous standard state, is suitable for determining if the conjugate acid, HL, of leaving group, L, has an aqueous pKa of greater than about 13 to less than about 17. However, it is restricted in that (1) it requires extrapolation across varying solvent media and (2) errors made in determining indicator $pK_a$ values are cumulative. For these and other reasons, Bordwell and co-workers have developed a scale of acidity in dimethylsulfoxide (DMSO). This solvent has the advantage of a relatively high dielectric constant ($\epsilon$=47); ions are therefore dissociated so that problems of differential ion pairing are reduced. Although the results are referred to a standard state in DMSO instead of in water, a link with the aqueous $pK_a$ scale has been made. When acidities measured in water or on a water-based scale are compared with those measured in DMSO, acids whose conjugate bases have their charge localized are stronger acids in water; acids whose conjugate bases have their charge delocalized over a large area are usually of comparable strength. Bordwell details his findings in a 1988 article (Acc. Chem. Res. 1988, 21, 456–463). Procedures for measurement of $pK_a$ in DMSO are found in papers referenced therein.

Definitions of $k_H$, kp, and $k_D$

In the expressions given below, the choice of whether to use the concentration of a nucleophile or of its anion in the rate equation was made as a matter of convenience. One skilled in the art will realize that measurement of solution pH provides a convenient means of directly measuring the concentration of hydroxide ions present. One skilled in the art will further recognize that use of the total concentrations of hydrogen peroxide and peracid provide the most convenient means to determine the rate constants kp and $k_D$.

The terms, such as RC(O)L, used in the following definitions and in the conditions for the determination of $k_H$, kp and $k_D$, are illustrative of a general bleach activator structure and are not limiting to any specific bleach activator structure herein.

Definition of $k_H$ $$RC(O)L + HO^- \rightarrow RC(O)O^- + HL$$

The rate of the reaction shown above is given by

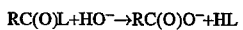

The rate constant for hydrolysis of bleach activator ($k_H$) is the second order rate constant for the bimolecular reaction between bleach activator and hydroxide anion as determined under the conditions specified below.

Definition of kp $$RC(O)L + H_2O_2 \rightarrow RC(O)O_2H + HL$$

The rate of the reaction shown above is given by

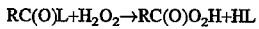

where $[H_2O_2]_T$ represents the total concentration of hydrogen peroxide and is equal to $[H_2O_2]+[HO_2^-]$.

The rate constant for perhydrolysis of bleach activator (kp) is the second order rate constant for the bimolecular reaction between bleach activator and hydrogen peroxide as determined under the conditions specified below.

Definition of $k_D$ $$RC(O)L + RC(O)O_2H \rightarrow RC(O)O_2C(O)R + HL$$

The rate of the reaction shown above is given by $$\text{Rate} = k_{D'}[RC(O)L][RC(O)O_2H]_T$$

where $[RC(O)O_2H]_T$ represents the total concentration of peracid and is equal to $[RC(O)O_2H] + [RC(O)O_2^-]$.

The rate constant for the formation of a diacylperoxide from the bleach activator ($k_D$), the second order rate constant for the bimolecular reaction between bleach activator and peracid anion, is calculated from the above defined $k_{D'}$. The value for $k_{D'}$ is determined under the conditions specified below.

Definition of Perhydrolysis Selectivity Coefficient

Perhydrolysis selectivity coefficient is defined as the ratio $Kp/K_D$ wherein Kp and $K_D$ are as defined as above.

CONDITIONS FOR THE DETERMINATION OF RATE CONSTANTS

Hydrolysis

A set of experiments is completed to measure the rate of hydrolysis of a bleach activator RC(O)L in aqueous solution at total ionic strength of 1M as adjusted by addition of NaCl. The temperature is maintained at 35.0°±0.1° C. and the solution is buffered with $NaHCO_3$+Na2CO_3$. A solution of the activator ([RC(O)L]=0.5 mM) is reacted with varying concentrations of NaOH under stopped-flow conditions and the rate of reaction is monitored optically. Reactions are run under pseudo first-order conditions to determine the bimolecular rate constant for hydrolysis of bleach activator ($k_H$). Each kinetic run is repeated at least five times with about eight different concentrations of hydroxide anions. All kinetic traces give satisfactory fits to a first-order kinetic rate law and a plot of the observed first-order rate constant versus concentration of hydroxide anion is linear over the region investigated. The slope of this line is the derived second order rate constant $k_H$.

Perhydrolysis

A set of experiments is completed to measure the rate of perhydrolysis of a bleach activator RC(O)L in aqueous solution at pH=10.0 with constant ionic strength of 1M as adjusted by addition of NaCl. The temperature is maintained at 35.0°±0.1° C. and the solution is buffered with $NaHCO_3$+$Na_2CO_3$. A solution of the activator ([RC(O)L]=0.5 mM) is reacted with varying concentrations of sodium perborate under stopped-flow conditions and the rate of reaction is monitored optically. Reactions are run under pseudo first-order conditions in order to determine the bimolecular rate constant for perhydrolysis of bleach activator (kp). Each kinetic run is repeated at least five times with about eight different concentrations of sodium perborate. All kinetic traces give satisfactory fits to a first-order kinetic rate law and a plot of the observed first-order rate constant versus total concentration of hydrogen peroxide is linear over the region investigated. The slope of this line is the derived second order rate constant kp. One skilled in the art recognizes that this rate constant is distinct from, but related to, the second order rate constant for the reaction of a bleach activator with the anion of hydrogen peroxide ($k_{nuc}$). The relationship of these rate constants is given by the following equation:

$$k_{nuc} = kp \{(K_a + [H^+])/K_a\}$$

where $K_a$ is the acid dissociation constant for hydrogen peroxide.

Formation of Diacylperoxide

A set of experiments is completed to measure the rate of formation of a diacylperoxide $RC(O)O_2C(O)R$ from a bleach activator RC(O)L in aqueous solution at pH=10.0 with constant ionic strength of 1M as adjusted by addition of NaCl. The temperature is maintained at 35.0°±0.1° C. and the solution is buffered with $NaHCO_3$+$Na_2CO_3$. A solution of the activator ([RC(O)L]=0.5 mM) is reacted with varying concentrations of peracid under stopped-flow conditions and the rate of reaction is monitored optically. Reactions are run under pseudo first-order conditions in order to determine the bimolecular rate constant $k_{D'}$. Each kinetic run is repeated at least five times with about eight different concentrations of peracid anion. All kinetic traces give satisfactory fits to a first-order kinetic rate law and a plot of the observed first-order rate constant versus total concentration of peracid is linear over the region investigated. The slope of this line is the derived second order rate constant $k_{D'}$. The bimolecular rate constant for the formation of a diacylperoxide from peracid anion ($k_D$) is calculated according to $$k_D = k_{D'}\{(K_a + [H^+])/K_a\}$$

where $K_a$ is the acid dissociation constant for the peracid $RC(O)O_2H$. One skilled in the art will realize that the $pK_a$ values for peracids fall into a rather narrow range from about 7 to about 8.5 and that at pH=10.0, when $K_a \geq$ about $10^{-8}$, $\{(K_a+[H^+])/K_a\} \cong 1$ and $k_D \cong k_{D'}$.

Test for Low pH Perhydrolysis Efficiency

This method is applicable as a test for screening any bleach activators RC(O)L (not intending to be limiting of any specific performance-enhanced bleach activator structure herein) by confirmation of the formation of peracid analyte $RC(O)O_2H$. The minimum standard for low pH perhydrolysis efficiency (LPE) is a coefficient, as defined below, $\geq 0.15$ within 10 minutes when tested under the conditions specified below.

Test Protocol

Distilled, deionized water (495 mL; adjusted to pH 7.5 with $NaH_2PO_4$ and $Na_2HPO_4$) is added to a 1000 mL beaker and heated to 40°±1° C. Three hundred seventy-five (375) mg of 30% concentration hydrogen peroxide is added to the beaker and the mixture is stirred for two minutes before a 5 mL solution containing 100 mg of activator (predissolved in 5 mL of an organic solvent (e.g. methanol or dimethylformamide)) is added. The initial data point is taken 1 minute thereafter. A second sample is removed at 10 minutes. Sample aliquots (2 mL) are examined via analytical HPLC for the quantitative determination of peracid $RC(O)O_2H$.

Sample aliquots are individually mixed with 2 mL of a pre-chilled 5° C. solution of acetonitrile/acetic acid ($^{86}/_{14}$) and placed in temperature controlled 5° C. autosampler for subsequent injection onto the HPLC column.

High performance liquid chromatography of the authentic peracid under a given set of conditions establishes the characteristic retention time ($t_R$) for the analyte. Conditions for the chromatography will vary depending on the peracid of interest and should be chosen so as to allow baseline separation of the peracid from other analytes. A standard calibration curve (peak area vs. concentration) is constructed using the peracid of interest. The analyte peak area of the 10 minute sample from the above described test is thereby converted to ppm peracid generated for determination of the quantity LPE. A bleach activator is considered acceptable when a value of the low pH perhydrolysis efficiency coefficient, LPE=[(ppm of peracid generated)/(theoretical ppm peracid)]≧0.15 is achieved within ten minutes under the specified test conditions.

To note, by comparison with 4,5-saturated cyclic amidine embodiments of the instant bleach activators, known closely related chemical compounds wherein the 4,5 position is unsaturated have surprisingly greater rates of hydrolysis. Specifically, acetyl imidazole has $k_H$ greater than $10.0 M^{-1} s^{-1}$: accordingly this invention does not encompass imidazole as a leaving group.

Bleaching Compositions

Effective bleach-additives herein may comprise the bleach activators of this invention without a hydrogen peroxide source, but pereferably include detergent surfactants and one or more members selected from the group consisting of low-foaming automatic dishwashing surfactants, ethoxylated nonionic surfactants, bleach stable thickeners, transition-metal chelants, builders, flourescent whitening agents (also known as brighteners), and buffering agents. However, for bleaching compositions, the bleach activators are not preferably employed alone but in combination with a source of hydrogen peroxide, as disclosed hereinafter. Levels of the bleach activators herein may vary widely, e.g., from about 0.1% to about 90%, by weight, of composition, although lower levels, e.g., from about 0.1% to about 30% are more typically used.

Source of Hydrogen Peroxide

A source of hydrogen peroxide herein is any convenient compound or mixture which under consumer use conditions provides an effective amount of hydrogen peroxide. Levels may vary widely and are typically from about 0.5% to about 70%, more typically from about 0.5% to about 25%, by weight of the bleaching compositions.

The source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Mixtures of any convenient hydrogen peroxide sources can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

Fully-formulated laundry and automatic dishwashing compositions typically will also comprise other adjunct ingredients to improve or modify performance. Typical, non-limiting examples of such ingredients are disclosed hereinafter for the convenience of the formulator.

ADJUNCT INGREDIENTS

Bleach Catalysts

If desired, the bleaches can be catalyzed by means of a manganese compound. Such compounds are well known in the art and include, for example, the manganese-based catalysts disclosed in U.S. Pat. Nos. 5,246,621, 5,244,594; 5,194,416; 5,114,606; and European Pat. App. Pub. Nos. 549,271A1, 549,272A1, 544,440A2, and 544,490A1; Preferred examples of these catalysts include $Mn^{IV}_2(u-O)_3(1,4,7\text{-trimethyl-1,4,7-triazacyclononane})_2\text{-}(PF_6)_2$, $Mn^{III}_2(u-O)_1(u-OAc)_2(1,4,7\text{-trimethyl-1,4,7-triazacyclononane})_2(ClO_4)_2$, $Mn^{IV}_4(u-O)_6(1,4,7\text{-triazacyclononane})_4(ClO_4)_4$, $Mn^{III}\text{-}Mn^{IV}_4\text{-}(u-O)_1(u-OAc)_2\text{-}(1,4,7\text{-trimethyl-}1,4,7\text{triazacyclo-nonane})_2\text{-}(ClO_4)_3$, $Mn^{IV}\text{-}(1,4,7\text{-trimethyl-1,4,7-triazacyclo-nonane})\text{-}(OCH_3)_3(PF_6)$, and mixtures thereof. Other metal-based bleach catalysts include those disclosed in U.S. Pat. No. 4,430,243 and U.S. Pat. No. 5,114,611. The use of manganese with various complex ligands to enhance bleaching is also reported in the following U.S. Pat. Nos.; 4,728,455; 5,284,944; 5,246,612; 5,256,779; 5,280,117; 5,274,147; 5,153,161; and 5,227,084.

Said manganese can be precomplexed with ethylenediaminedisuccinate or separately added, for example as a sulfate salt, with ethylenediaminedisuccinate. (See U.S. application Ser. No. 08/210,186, filed Mar. 17, 1994.) Other preferred transition metals in said transition-metal-containing bleach catalysts include iron or copper.

Remarkably, preferred embodiments of the present invention in which the wash pH is in the range from about 6.5 to about 9.5 and there is present one of the above-indicated selected performance-enhanced bleach activators in combination with one of the above-indicated bleach catalysts, secure a particularly superior bleaching effect as compared with otherwise identical compositions in which conventional bleach activators such as TAED (see hereinbelow) are used in place of the performance-enhanced bleach activator.

As a practical matter, and not by way of limitation, bleaching solutions of this invention may comprise at least one part per ten million of the active bleach catalyst species in the aqueous washing liquor, and will preferably provide from about 0.1 ppm to about 700 ppm, more preferably from about 1 ppm to about 50 ppm, of the catalyst species in the laundry liquor.

Conventional Bleach Activators

"Conventional bleach activators" herein are any bleach activators which do not respect the above-identified provisions given in connection with the performance-boosting bleach activators. Numerous conventional bleach activators are known and are optionally included in the instant bleaching compositions. Various nonlimiting examples of such activators are disclosed in U.S. Pat. No. 4,915,854, issued Apr. 10, 1990 to Mao et al, and U.S. Pat. No. 4,412,934. The nonanoyloxybenzene sulfonate (NOBS) and tetraacetyl ethylenediamine (TAED) activators are typical, and mixtures thereof can also be used. See also U.S. Pat. No. 4,634,551 for other typical conventional bleach activators. Known amido-derived bleach activators are those of the formulae: $R^1N(R^5)C(O)R^2C(O)L$ or $R^1C(O)N(R^5)R^2C(O)L$ wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. Further illustration of optional, conventional bleach activators of the above formulae include (6-octanamidocaproyl)oxybenzenesulfonate, (6-nonanamidocaproyl)-oxybenzenesulfonate, (6-decanamido-caproyl)oxybenzenesulfonate, and mixtures thereof as described in U.S. Pat. No. 4,634,551. Another class of conventional bleach activators comprises the benzoxazin-type activators disclosed by Hodge et al in U.S. Pat. No. 4,966,723, issued Oct. 30, 1990. Still another class of conventional bleach activators includes those acyl lactam activators which do not provide the benefits and criticalities described herein. Examples of optional lactam activators include octanoyl caprolactam, 3,5,5-trimethylhexanoyl caprolactam, nonanoyl caprolactam, decanoyl caprolactam, undecenoyl caprolactam, octanoyl valerolactam, decanoyl valerolactam, undecenoyl valerolactam, nonanoyl valerolactam, 3,5,5-trimethylhexanoyl valerolactam and mixtures thereof.

Bleaching agents other than hydrogen peroxide sources are also known in the art and can be utilized herein as adjunct ingredients. One type of non-oxygen bleaching agent of particular interest includes photoactivated bleaching agents such as the sulfonated zinc and/or aluminum phthalocyanines. See U.S. Pat. No. 4,033,718, issued Jul. 5, 1977 to Holcombe et al. If used, detergent compositions will typically contain from about 0.025% to about 1.25%, by weight, of such bleaches, especially sulfonated zinc phthalocyanine.

Organic Peroxides, Especially Diacyl Peroxides are extensively illustrated in Kirk Othmer, Encyclopedia of Chemical Technology, Vol. 17, John Wiley and Sons, 1982 at pages 27–90 and especially at pages 63–72, all incorporated herein by reference. Suitable organic peroxides, especially diacyl peroxides, are further illustrated in "Initiators for Polymer Production", Akzo Chemicals Inc., Product Catalog, Bulletin No. 88–57, incorporated by reference. Preferred diacyl peroxides herein whether in pure or formulated form for granule, powder or tablet forms of the bleaching compositions constitute solids at 25° C., e.g., CADET® BPO 78 powder form of dibenzoyl peroxide, from Akzo. Highly preferred organic peroxides, particularly the diacyl peroxides, for such bleaching compositions have melting points above 40° C., preferably above 50° C. Additionally, preferred are the organic peroxides with SADT's (as defined in the foregoing Akzo publication) of 35° C. or higher, more preferably 70° C. or higher. Nonlimiting examples of diacyl peroxides useful herein include dibenzoyl peroxide, lauroyl peroxide, and dicumyl peroxide. Dibenzoyl peroxide is preferred. In some instances, diacyl peroxides are available in the trade which contain oily substances such as dioctyl phthalate. In general, particularly for automatic dishwashing applications, it is preferred to use diacyl peroxides which are substantially free from oily phthalates since these can form smears on dishes and glassware.

Quaternary Substituted Bleach Activators

The present bleaching solutions or compositions useful therein can optionally further comprise conventional, known quaternary substituted bleach activators (QSBA). QSBA's are further illustrated in U.S. Pat. No. 4,539,130, Sep. 3, 1985 and U.S. Pat. No. 4,283,301. British Pat. 1,382,594, published Feb. 5, 1975, discloses a class of QSBA's optionally suitable for use herein. U.S. Pat. No. 4,818,426 issued Apr. 4., 1989 discloses another class of QSBA's. Also see U.S. Pat. No. 5,093,022 issued Mar. 3, 1992 and U.S. Pat. No. 4,904,406, issued Feb. 27, 1990. Additionally, QSBA's are described in EP 552,812 A1 published Jul. 28, 1993, and in EP 540,090 A2, published May 5, 1993.

Detersive Surfactants

Surfactants are useful herein for their usual cleaning power and may be included in preferred embodiments of the instant compositions at the usual detergent-useful levels. Such combinations are better than the surfactant-free counterparts in terms of overall cleaning and bleaching performance and are possibly synergistic.

Nonlimiting examples of surfactants useful herein include the conventional $C_{11}$–$C_{18}$ alkylbenzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3-M^+)CH_3$ and $CH_3(CH_2)_y(CHOSO_3-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10}$–$C_{18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxylate/propoxylates), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Automatic dishwashing compositions typically employ low sudsing surfactants, such as the mixed ethyleneoxy/propyleneoxy nonionics. Other conventional useful surfactants are listed in standard texts.

Builders

Detergent builders can optionally be included in the compositions useful herein to assist in controlling mineral hardness. Inorganic as well as organic builders can be used. Builders are typically used in automatic dishwashing and fabric laundering compositions to assist in the removal of particulate soils.

The level of builder can vary widely depending upon the end use of the composition and its desired physical form. When present, the compositions will typically comprise at least about 1% builder. High performance compositions typically comprise from about 10% to about 80%, more typically from about 15% to about 50% by weight, of the detergent builder. Lower or higher levels of builder, however, are not excluded.

Inorganic or P-containing detergent builders include, but are not limited to, the alkali metal, ammonium and alkanolammonium salts of polyphosphates (exemplified by the tripolyphosphates, pyrophosphates, and glassy polymeric metaphosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt"

situation that may occur with zeolite or layered silicate builders. See U.S. Pat. No. 4,605,509 for examples of preferred aluminosilicates.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6® is a crystalline layered silicate marketed by Hoechst (commonly abbreviated herein as "SKS-6"). Unlike zeolite builders, the Na SKS-6 silicate builder does not contain aluminum. NaSKS-6 is the $\delta$-$Na_2SiO_5$ morphology form of layered silicate and can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the $\alpha$-, $\beta$- and $\gamma$-forms. Other silicates may also be useful, such as for example magnesium silicate, which can serve as a crispening agent in granular formulations, as a stabilizing agent for oxygen bleaches, and as a component of suds control systems.

Silicates useful in automatic dishwashing (ADD) applications include granular hydrous 2-ratio silicates such as BRITESIL® H20 from PQ Corp., and the commonly sourced BRITESIL® H24 though liquid grades of various silicates can be used when the ADD composition has liquid form. Within safe limits, sodium metasilicate or sodium hydroxide alone or in combination with other silicates may be used in an ADD context to boost wash pH to a desired level.

Examples of carbonate builders are the alkaline earth and alkali metal carbonates as disclosed in German Patent Application No. 2,321,001 published on Nov. 15, 1973. Various grades and types of sodium carbonate and sodium sesquicarbonate may be used, certain of which are particularly useful as carriers for other ingredients, especially detersive surfactants.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula: $[M_z(zAlO_2) y] \cdot xH_2O$ wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula: $Na_{12}[(AlO_2)_{12}(SiO_2)_{12}] \cdot xH_2O$ wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter. As with other builders such as carbonates, it may be desirable to use zeolites in any physical or morphological form adapted to promote surfactant carrier function, and appropriate particle sizes may be freely selected by the formulator.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt or "overbased". When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediaminetetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty laundry detergent formulations due to their availability from renewable resources and their biodegradability. Citrates can also be used in combination with zeolite and/or layered silicate builders. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Chelating Agents

The compositions useful herein may also optionally contain one or more iron and/or manganese chelating agents, such as diethylenetriaminepenta acetic acid (DTPA). More generally, chelating agents suitable for use herein can be selected from the group consisting of aminocarboxylates, aminophosphonates, polyfunctionally-substituted aromatic chelating agents and mixtures thereof. Without intending to be bound by theory, it is believed that the benefit of these materials is due in part to their exceptional ability to remove iron and manganese ions from washing solutions by formation of soluble chelates; other benefits include inorganic film or scale prevention. Other suitable chelating agents for use herein are the commercial DEQUEST® series, and chelants from Monsanto, DuPont, and Nalco, Inc.

Aminocarboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

Aminophosphonates are also suitable for use as chelating agents in the compositions of the invention when at least low levels of total phosphorus are permitted in detergent compositions, and include ethylenediaminetetrakis (methylenephosphonates). Preferably, these aminophosphonates do not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A highly preferred biodegradable chelator for use herein is ethylenediamine disuccinate ("EDDS"), especially (but not limited to) the [S,S] isomer as described in U.S. Pat. No. 4,704,233, Nov. 3, 1987, to Hartman and Perkins. The trisodium salt is preferred though other forms, such as magnesium salts, may also be useful.

If utilized, especially in ADD compositions, these chelating agents or transition-metal-selective sequestrants will preferably comprise from about 0.001% to about 10%, more preferably from about 0.05% to about 1% by weight of the bleaching compositions herein.

Enzymes

Enzymes can be included in the formulations herein for a wide variety of fabric laundering or other cleaning purposes, including removal of protein- based, carbohydrate-based, or triglyceride-based stains, for example, and for the prevention of refugee dye transfer, and for fabric restoration. The enzymes to be incorporated include proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders, etc.. In this respect bacterial or fungal enzymes are preferred, such as bacterial amylases and proteases, and fungal cellulases.

Enzymes are normally incorporated at levels sufficient to provide up to about 5 mg by weight, more typically about 0.01 mg to about 3 mg, of active enzyme per gram of the composition. Stated otherwise, the compositions herein will typically comprise from about 0.001% to about 5%, preferably 0.01%–1% by weight of a commercial enzyme preparation. Protease enzymes are usually present in such commercial preparations at levels sufficient to provide from 0.005 to 0.1 Anson units (AU) of activity per gram of composition.

Suitable examples of proteases are the subtilisins which are obtained from particular strains of B. subtilis and B. licheniformis. Another suitable protease is obtained from a strain of Bacillus, having maximum activity throughout the pH range of 8–12, developed and sold by Novo Industries A/S as ESPERASE®. The preparation of this enzyme and analogous enzymes is described in British Patent Specification No. 1,243,784 of Novo. Proteolytic enzymes suitable for removing protein-based stains that are commercially available include those sold under the tradenames ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985) and Protease B (see European Patent Application Serial No. 87303761.8, filed Apr. 28, 1987, and European Patent Application 130,756, Bott et al, published Jan. 9, 1985).

An especially preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76 in combination with one or more amino acid residue positions equivalent to those selected from the group consisting of +99, +101, +103, +107 and +123 in *Bacillus amyloliquefaciens* subtilisin as described in the patent applications of A. Baeck, C. K. Ghosh, P. P. Greycar, R. R. Bott and L. J. Wilson, entitled "Protease-Containing Cleaning Compositions" having U.S. Ser. No. 08/136,797 (P&G Case 5040), and "Bleaching Compositions Comprising Protease Enzymes" having U.S. Ser. No. 08/136,626.

Amylases include, for example, α-amylases described in British Patent Specification No. 1,296,839 (Novo), RAPIDASE®, International Bio-Synthetics, Inc. and TERMAMYL®, Novo Industries.

Cellulases usable in the present invention include both bacterial or fungal cellulases. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from *Humicola insolens* and *Humicola* strain DSM1800 or a cellulase 212-producing fungus belonging to the genus *Aeromonas*, and cellulase extracted from the hepatopancreas of a marine mollusk (*Dolabella Auricula Solander*). Suitable cellulases are also disclosed in GB-A-2.075.028; GB-A-2.095.275 and DE-OS-2.247.832. CAREZYME® (Novo) is especially useful.

Suitable lipase enzymes for detergent use include those produced by microorganisms of the *Pseudomonas* group, such as *Pseudomonas stutzeri* ATCC 19.154, as disclosed in British Patent 1,372,034. See also lipases in Japanese Patent Application 53,20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex *Chromobacter viscosum*, e.g. *Chromobacter viscosum var. lipolyticum* NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*. The LIPOLASE® enzyme derived from *Humicola lanuginosa* and commercially available from Novo (see also EPO 341,947) is a preferred lipase for use herein.

Peroxidase enzymes can be used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

Other Ingredients

Usual detersive ingredients can include one or more other detersive adjuncts or other materials for assisting or enhancing cleaning performance, treatment of the substrate to be cleaned, or to modify the aesthetics of the detergent composition. Usual detersive adjuncts of detergent compositions include the ingredients set forth in U.S. Pat. No. 3,936,537, Baskerville et al. Adjuncts which can also be included in detergent compositions employed in the present invention, in their conventional art-established levels for use (generally from 0% to about 20% of the detergent ingredients, preferably from about 0.5% to about 10%), include other active ingredients such as dispersant polymers from BASF Corp. or Rohm & Haas; color speckles, anti-tarnish and/or anti-corrosion agents, dyes, fillers, optical brighteners, germicides, alkalinity sources, hydrotropes, anti-oxidants, enzyme stabilizing agents, perfumes, solubilizing agents, clay soil removlval/anti-redeposition agents, carders, processing aids, pigments, solvents for liquid formulations, fabric softeners, static control agents, solid fillers for bar compositions, etc. Dye transfer inhibiting agents, including polyamine N-oxides such as polyvinylpyridine N-oxide can be used. Dye-transfer-inhibiting agents are further illustrated by polyvinylpyrrolidone and copolymers of N-vinyl imidazole and N-vinyl pyrrolidone. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanoi amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, 0.1%–2%, to provide additional suds and to enhance grease removal performance.

Brightener

Any optical brighteners or other brightening or whitening agents known in the art can be incorporated at levels typically from about 0.05% to about 1.2%, by weight, into the detergent compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, N.Y. (1982).

Specific examples of optical brighteners which are useful in the present compositions are those identified in U.S. Pat. No. 4,790,856, issued to Wixon on Dec. 13, 1988. These brighteners include the PHORWHITE series of brighteners from Verona. Other brighteners disclosed in this reference include: Tinopal UNPA, Tinopal CBS and Tinopal 5 BM; available from Ciba-Geigy; Artic White CC and Artic White CWD, available from Hilton-Davis, located in Italy; the 2-(4-stryl-phenyl)-2H-napthol[1,2-d]triazoles; 4,4'-bis-(1,2,3-triazol-2-yl)-stil- benes; 4,4'-bis(stryl)bisphenyls; and the aminocoumarins. Specific examples of these brighteners include 4-methyl-7-diethyl- amino coumarin; 1,2-bis(-venzimidazol-2-yl)ethylene; 1,3-diphenyl-phrazolines; 2,5-bis(benzoxazol-2-yl)thiophene; 2-strylnapth-[1,2-d]oxazole; and 2-(stilbene-4-yl)-2H-naphtho- [1,2-d]triazole. See also U.S. Pat. No. 3,646,015, issued Feb. 29, 1972 to Hamilton. Anionic brighteners are preferred herein.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT® D10, Degussa) is admixed with a proteolytic enzyme solution containing 3%–5% of $C_{13}$-15 ethoxylated alcohol (EO 7) nonionic surfactant. Typically, the enzyme/surfactant solution is 2.5 X the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Liquid or gel compositions can contain some water and other fluids as carders. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carders.

Certain bleaching compositions herein among the generally encompassed liquid (easily flowable or gel forms) and solid (powder, granule or tablet) forms, especially bleach additive compositions and hard surface cleaning compositions, may preferably be formulated such that the pH is acidic during storage and alkaline during use in aqueous cleaning operations, i.e., the wash water will have a pH in the range from about 7 to about 11.5. Laundry and automatic dishwashing products are typically at pH 7–12, preferably 9 to 11.5. Automatic dishwashing compositions, other than rinse aids which may be acidic, will typically have an aqueous solution pH greater than 7. Techniques for controlling pH at recommended usage levels include the use of buffers, alkalis, acids, pH-jump systems, dual compartment containers, etc., and are well known to those skilled in the art. The compositions are useful from about 5° C. to the boil for a variety of cleaning and bleaching operations.

Bleaching compositions in granular form typically limit water content, for example to less than about 7% free water, for best storage stability.

Storage stability of bleach compositions can be further enhanced by limiting the content in the compositions of adventitious redox-active substances such as rust and other traces of transition metals in undesirable form. Certain bleaching compositions may moreover be limited in their total halide ion content, or may have any particular halide, e.g., bromide, substantially absent. Bleach stabilizers such as stannates can be added for improved stability and liquid formulations may be substantially nonaqueous if desired.

The following examples illustrate the bleach activators useful in this invention, intermediates for making same and bleaching compositions which can be prepared using the bleach activators, but are not intended to be limiting thereof. All materials in Examples I-XXX satisfy the functional limitations herein.

EXAMPLE I

N-[(4-methylsulfonyl)benzoyl] Caprolactam

All glassware is dried thoroughly, and the reaction kept under an inert atmosphere (argon) at all times.

With stirring, 5.0 g (25.0 mmol) of (4-methylsulfonyl) benzoic acid (Aldrich) and 5.5 mL (75.0 mmol) of thionyl chloride (Aldrich, d=1.631 g/mol) are added to 100 mL tetrahydrofuran (THF—Aldrich, HPLC grade) in a 3-neck round bottom flask equipped with a reflux condenser, addition funnel, and magnetic stirrer. The resulting reaction mixture is heated to reflux and stirred for 16 h. After cooling to room temperature, the solvent and excess thionyl chloride are removed by evaporation under reduced pressure. Recrystallization of the solid residue from toluene followed by drying under high vacuum yields pure (4-methylsulfonyl) benzoyl chloride as a white, crystalline solid.

In a subsequent reaction, 2.33 g (20.6 mmol) of caprolactam (Aldrich) and 2.30 g (22.7 mmol) of triethylamine (Aldrich, d=0.726 g/mol) are added to 50 mL THF (Aldrich, HPLC grade) in a 3-neck round bottom flask equipped with a reflux condenser, addition funnel, and magnetic stirrer. Addition of a solution of 4.50 g (20.6 mmol) of the (4-methylsulfonyl)-benzoyl chloride in 50 mL Tiff proceeds dropwise over a period of 30 min, and the resulting reaction mixture is heated to reflux and stirred for 16 h. Upon cooling to room temperature, the TI-IF is removed by evaporation under reduced pressure. The solid residue is redissolved in chloroform, and extracted several times with D.I. water. The organic layer is dried over $Na_2SO_4$, filtered, concentrated by removal of solvent, and poured into hexane to precipitate the product. The precipitate is collected by suction filtration, rinsed with hexane, and dried under vacuum to yield N-[(4-methylsulfonyl)benzoyl] caprolactam as a white, crystalline solid.

EXAMPLE II

N-[(4-methylsulfonyl)benzoyl]valerolactam

Synthesized as for N-[(4-methylsulfonyl)benzoyl] caprolactam (Example I) using valerolactam (Aldrich) in place of caprolactam.

EXAMPLE III

N-[(4-ethylsulfonyl)benzoyl]caprolactam

The synthesis of N-[(4-ethylsulfonyl)benzoyl] caprolactam proceeds as for N-[(4-methylsulfonyl)benzoyl] caprolactam (Example I) using (4-ethylsulfonyl)benzoic acid in place of(4-methylsulfonyl)benzoic acid.

The (4-ethylsulfonyl)benzoic acid can be synthesized from 2-chloropropionic acid and 4-(chlorosulfonyl)benzoic acid according to the procedure of Brown, R. W. *J. Org. Chem.* 1991, 56, 4974–4976.

EXAMPLE IV

N-[(4-ethylsulfonyl)benzoyl]valerolactam

Synthesized as for N-[(4-ethylsulfonyl)benzoyl] caprolactam (Example III) using valerolactam (Aldrich) in place of caprolactam.

EXAMPLE V

N-[(4-pentylsulfonyl)benzoyl]caprolactam

Synthesized as for N-[(4-ethylsulfonyl)benzoyl] caprolactam (Example III) using 2-bromohexanoic acid (Aldrich) in place of 2-chloropropionic acid.

EXAMPLE VI

N-[(4-pentylsulfonyl)benzoyl]valerolactam

Synthesized as for N-[(4-pentylsulfonyl)benzoyl] caprolactam (Example V) using valerolactam (Aldrich) in place of caprolactam.

EXAMPLE VII

N-[(4-heptysulfonyl)benzoyl]caprolactam

Synthesized as for N-[(4-ethylsulfonyl)benzoyl] caprolactam (Example III) using 2-bromooctanoic acid (Aldrich) in place of 2-chloropropionic acid.

EXAMPLE VIII

N-[(4-heptylsulfonyl)benzoyl]valerolactam

Synthesized as for N-[(4-heptylsulfonyl)benzoyl] caprolactam (Example VII) using valerolactam (Aldrich) in place of caprolactam.

EXAMPLE IX

N-(2-furoyl)valerolactam

All glassware is dried thoroughly, and the reaction is kept under an inert atmosphere (argon) at all times. With stirring, 20.0 g (0.18 mol) of 2-furoic acid (Aldrich) and 40.0 mL (0.53 mol) of thionyl chloride (Aldrich, d=1.631 g/mol) are added to 300 mL THF (Aldrich, HPLC grade) in a single-neck round bottom flask equipped with a reflux condenser and magnetic stirrer. The resulting reaction mixture is heated to reflux and stirred for 16 h. After cooling to room temperature, the solvent and excess thionyl chloride are removed by evaporation under reduced pressure to yield 2-furoyl chloride. In a subsequent reaction, 9.2 g (92 mmol) of valerolactam (Aldrich) and 14.1 mL (101 mmol) of triethylamine (Aldrich, d=0.726 g/mol) are added to 150 mL THF (Aldrich, HPLC grade) in a 3-neck round bottom flask equipped with a reflux condenser, addition funnel, and magnetic stirrer. Addition of a solution of 12.0 g (92 mmol) of the 2-furoyl chloride in 150 mL THF proceeds dropwise over a period of 30 min, and the resulting reaction mixture is heated to reflux and stirred for 16 h. Upon cooling to room temperature, the THF is removed by evaporation under reduced pressure. The solid residue is redissolved in methylene chloride, and extracted several times with 5% aqueous hydrochloric and then deionized water. The organic layer is dried over $Na_2SO_4$, filtered, concentrated by removal of solvent, and poured into hexane to precipitate the product. The precipitate is collected by suction filtration, rinsed with hexane, and dried under vacuum to yield N-(2-furoyl) valerolactam as a white, crystalline solid.

EXAMPLE X

N-(2-furoyl)caprolactam

Synthesized as for N-(2-furoyl)valerolactam (Example IX) using caprolactam (Aldrich) in place of valerolactam.

EXAMPLE XI

N-(3-furoyl)caprolactam

Synthesized as for N-(2-furoyl)caprolactam (Example X) using 3-furoic acid in place of 2-furoic acid.

EXAMPLE XII

N-(3-furoyl)valerolactam

Synthesized as for N-(3-furoyl)caprolactam (Example XI) using valerolactam (Aldrich) in place of caprolactam.

EXAMPLE XIII

N-(5-nitro-2-furoyl)caprolactam

Synthesized as for N-(2-furoyl)caprolactam (Example XI) using 5-nitro-2-furoic acid in place of 2-furoic acid.

EXAMPLE XIV

N-(5-nitro-2-furoyl)valerolactam

Synthesized as for N-(5-nitro-2-furoyl)caprolactam (Example XIII) using valerolactam (Aldrich) in place of caprolactam.

EXAMPLE XV

N-(5-bromo-2-furoyl) caprolactam

Synthesized as for N-(2-furoyl)caprolactam (Example X) using 5-bromo-2-furoic acid in place of 2-furoic acid.

EXAMPLE XVI

N-(5-bromo-2-furoyl)valerolactam

Synthesized as for N-(5-bromo-2-furoyl)caprolactam (Example XV) using valerolactam (Aldrich) in place of caprolactam.

EXAMPLE XVII

N-(1-naphthoyl)caprolactam

Synthesized as for N-(2-furoyl)caprolactam (Example X) using 1-naphthoic acid in place of 2-furoic acid.

EXAMPLE XVIII

N-(1-naphthoyl)valerolactam

Synthesized as for N-(1-naphthoyl)caprolactam (Example XVII) using valerolactam (Aldrich) in place of caprolactam.

EXAMPLE XIX

N-(3,5-dinitrobenzoyl) caprolactam

All glassware is dried thoroughly, and the reaction is kept under an inert atmosphere (argon) at all times. With stirring, 2.33 g (20.6 mmol) of caprolactam (Aldrich) and 2.30 g (22.7 mmol) of triethylamine (Aldrich, d=0.726 g/mol) are added to 100 mL toluene (Aldrich) in a 3-neck round bottom flask equipped with a reflux condenser, addition funnel, and mechanical stirrer, to give a clear, pale yellow solution. Addition of a solution of 4.75 g (20.6 mmol) of 3,5-dinitrobenzoyl chloride (Aldrich) in 100 mL toluene proceeds dropwise over a period of 30 min. The resulting reaction mixture is heated to reflux and stirred for 16 h. Upon cooling to room temperature, the reaction is filtered to remove the triethylamine hydrochloride, and poured into a separatory funnel. After dilution with 300 mL of chloroform, the organic solution is extracted with 5% aq HCl, 5% aq NaOH, and finally D.I. water. The organic layer is dried over $Na_2SO_4$, filtered, and the solvent removed by evaporation under reduced pressure. Recrystallization of the crude product from toluene followed by drying under vacuum yields N-(3,5-dinitrobenzoyl)caprolactam as a light yellow, crystalline solid.

EXAMPLE XX

N-(3,5-dinitrobenzoyl)valerolactam

Synthesized as for N-(3,5-dinitrobenzoyl)caprolactam (Example XIX) using valerolactam (Aldrich) in place of caprolactam.

EXAMPLE XXI

N-(3,5-dichlorobenzoyl)caprolactam

Synthesized as for N-(4-nitrobenzoyl)caprolactam (Example XXIII) using 3,5-dichlorobenzoylchloride (Aldrich) in place of 4-nitrobenzoyl chloride.

EXAMPLE XXII

N-(3,5-dichlorobenzoyl)valerolactam

Synthesized as for N-(3,5-dichlorobenzoyl)caprolactam (Example XXI) using valerolactam (Aldrich) in place of caprolactam.

Examples XXIII–XXX exemplify methods for synthesizing compounds generically disclosed in prior references.

EXAMPLE XXIII

N-(4-nitrobenzoyl)caprolactam

All glassware is dried thoroughly, and the reaction is kept under an inert atmosphere (argon) at all times. With stirring, 43.0 g (0.38 mol) of caprolactam (Aldrich) and 58.2 mL (0.42 mol) of triethylamine (Aldrich, d=0.726 g/mol) is added to 150 mL THF (Aldrich, HPLC grade) in a 3-neck round bottom flask equipped with a reflux condenser, addition funnel, and mechanical stirrer, to give a clear, pale yellow solution. Addition of a solution of 70.5 g (0.38 mol) of 4-nitrobenzoyl chloride (Aldrich) in 100 mL THF proceeds dropwise over a period of 1 h. The cloudy, dark yellow reaction mixture is heated to reflux and stirred for 16 h.

Upon cooling to room temperature, the reaction is filtered to remove the triethylamine hydrochloride, and poured into a separatory funnel. After dilution with chloroform, the organic solution is extracted twice 5% aq HCl, twice with 5% aq NaOH, and finally once with neutral D.I. water. The organic layer is dried over $Na_2SO_4$ or $MgSO_4$, filtered, and the solvent removed by evaporation under reduced pressure. Recrystallization of the crude product from toluene followed by drying under vacuum yields N-(4-nitrobenzoyl) caprolactam as a light yellow, crystalline solid.

EXAMPLE XXIV

N-(4-nitrobenzoyl)valerolactam

Synthesized as for N-(4-nitrobenzoyl)caprolactam (Example XXIII) using valerolactam (Aldrich) in place of caprolactam.

EXAMPLE XXV

N-(3-nitrobenzoyl)caprolactam

Synthesized as for N-(4-nitrobenzoyl)caprolactam (Example XXIII) using 3-nitrobenzoyl chloride (Aldrich) in place of 4-nitrobenzoyl chloride.

EXAMPLE XXVI

N-(3-nitrobenzoyl)valerolactam

Synthesized as for N-(3-nitrobenzoyl)caprolactam (Example XXV) using valerolactam (Aldrich) in place of caprolactam.

EXAMPLE XXVII

N-(3-chlorobenzoyl)caprolactam

Synthesized as for N-(4-nitrobenzoyl)caprolactam (Example XXIII) using 3-chlorobenzoyl chloride (Aldrich) in place of 4-nitrobenzoyl chloride.

EXAMPLE XXVIII

N-(3-chlorobenzoyl)valerolactam

Synthesized as for N-(3-chloroobenzoyl)caprolactam (Example XXVII) using valerolactam (Aldrich) in place of caprolactam.

EXAMPLE XXIX

N-(4-chlorobenzoyl)caprolactam

Synthesized as for N-(4-nitrobenzoyl)caprolactam (Example XXIII) using 4-chlorobenzoylchloride (Aldrich) in place of 4-nitrobenzoyl chloride.

EXAMPLE XXX

N-(4-chlorobenzoyl) valerolactam

Synthesized as for N-(4-chlorobenzoyl)caprolactam (Example XXIX) using valerolactam (Aldrich) in place of caprolactam.

EXAMPLE XXXI

Bleaching solutions useful for laundering fabrics are prepared by a step of mixing with water compositions having the form of granular laundry detergents

| INGREDIENT | A % | B % | C % | D % | E % |
|---|---|---|---|---|---|
| Bleach Activator* | 5 | 5 | 3 | 3 | 8 |
| Sodium Percarbonate | 0 | 0 | 19 | 21 | 0 |
| Sodium Perborate monohydrate | 21 | 0 | 0 | 0 | 20 |
| Sodium Perborate tetrahydrate | 12 | 21 | 0 | 0 | 0 |
| Tetraacetylethylenediamine | 0 | 0 | 0 | 1 | 0 |
| Nonanoyloxybenzenesulfonate | 0 | 0 | 3 | 0 | 0 |
| Linear alkylbenzenesulfonate | 7 | 11 | 19 | 12 | 8 |
| Alkyl ethoxylate (C45E7) | 4 | 0 | 3 | 4 | 6 |
| Zeolite A | 20 | 20 | 7 | 17 | 21 |
| SKS-6 ® silicate (Hoechst) | 0 | 0 | 11 | 11 | 0 |
| Trisodium citrate | 5 | 5 | 2 | 3 | 3 |
| Acrylic Acid/Maleic Acid copolymer | 4 | 0 | 4 | 5 | 0 |
| Sodium polyacrylate | 0 | 3 | 0 | 0 | 3 |
| Diethylenetriamine penta(methylene phosphonic acid) | 0.4 | 0 | 0.4 | 0 | 0 |
| DTPA | 0 | 0.4 | 0 | 0 | 0.4 |
| EDDS | 0 | 0 | 0 | 0.3 | 0 |
| Carboxymethylcellulose | 0.3 | 0 | 0 | 0.4 | 0 |
| Protease | 1.4 | 0.3 | 1.5 | 2.4 | 0.3 |
| Lipolase | 0.4 | 0 | 0 | 0.2 | 0 |
| Carezyme | 0.1 | 0 | 0 | 0.2 | 0 |
| Anionic soil release polymer | 0.3 | 0 | 0 | 0.4 | 0.5 |
| Dye transfer inhibiting polymer | 0 | 0 | 0.3 | 0.2 | 0 |
| Carbonate | 16 | 14 | 24 | 6 | 23 |
| Silicate | 3.0 | 0.6 | 12.5 | 0 | 0.6 |
| Sulfate, Water, Perfume, Colorants | to 100 | to 100 | to 100 | to 100 | to 100 |

*Bleach activator according to any of Examples I–XXX

The bleaching solutions are prepared by a step of mixing any of the above compositions with water, typically yielding a concentration of the composition of about 1000 ppm. These bleaching solutions can be used in a subsequent step to launder fabrics under "high soil" conditions. "High soil" conditions are achieved in either of two possible modes. In a first mode, consumer bundles of heavily soiled fabrics can be used, the soil level being sufficiently high that when a portion of the composition is dissolved in the presence of tap-water together with the soiled fabrics in a U.S. domestic washing-machine, the pH of the wash water is in the range from about pH 6.5 to about 9.5, more typically from about 7 to about 9.5. Alternatively, it is convenient for testing purposes when heavily soiled fabrics are unavailable, to use the following procedure: the pH of the wash bath after dissolution of product and addition of the test fabrics is adjusted using aqueous HCl such that the pH is in the range from about pH 6.5 to about 9.5. The test fabrics are a lightly soiled or clean bundle of consumer fabrics; additional test swatches of fabric comprising bleachable stains are typically added.

The laundering step typically involves washing fabrics at about 40° C., with excellent bleaching results, particularly with respect to bleaching as compared with otherwise identical compositions in which TAED, NOBS or benzoylcaprolactam are used at equal weight as a replacement for the performance-enhanced bleach activator. In particular, novel performance-enhanced bleach activators such as those of Examples III–XII provide superior results and are highly preferred.

Additional bleaching solutions can be prepared by a step of mixing with water of granular laundry detergents having nonionic surfactant systems as exemplified by the following formulations. These bleaching solutions can be used in a subsequent step to launder fabrics as described supra.

| INGREDIENT | F % | G % | H % | I % |
| --- | --- | --- | --- | --- |
| Bleach Activator* | 5 | 3 | 6 | 4.5 |
| Sodium Percarbonate | 20 | 21 | 21 | 21 |
| Tetraacetylethylenediamine | 0 | 6 | 0 | 0 |
| Nonanoyloxybenzenesulfonate | 4.5 | 0 | 0 | 4.5 |
| Alkyl ethoxylate (C45E7) | 2 | 5 | 5 | 5 |
| N-cocoyl N-methyl glucamine | 0 | 4 | 5 | 5 |
| Zeolite A | 6 | 5 | 7 | 7 |
| SKS-6 ® silicate (Hoechst) | 12 | 7 | 10 | 10 |
| Trisodium citrate | 8 | 5 | 3 | 3 |
| Acrylic Acid/Maleic Acid copolymer (partially neutralized) | 7 | 5 | 7 | 8 |
| Diethylenetriamine penta-(methylene phosphonic acid) | 0.4 | 0 | 0 | 0 |
| EDDS | 0 | 0.3 | 0.5 | 0.5 |
| Carboxymethylcellulose | 0 | 0.4 | 0 | 0 |
| Protease | 1.1 | 2.4 | 0.3 | 1.1 |
| Lipolase | 0 | 0.2 | 0 | 0 |
| Carezyme | 0 | 0.2 | 0 | 0 |
| Anionic soil release polymer | 0.5 | 0.4 | 0.5 | 0.5 |
| Dye transfer inhibiting polymer | 0.3 | 0.02 | 0 | 0.3 |
| Carbonate | 21 | 10 | 13 | 14 |
| Sulfate, Water, Perfume, Colorants | to 100 | to 100 | to 100 | to 100 |

*Bleach activator according to any of Examples I to XXX.

EXAMPLE XXXII

This Example illustrates bleaching solutions prepared by a step of mixing, with water, cleaning compositions having bleach additive form, more particularly, liquid bleach additive compositions.

| Ingredients | A wt % | B wt % | C wt % | D wt % |
| --- | --- | --- | --- | --- |
| NEODOL 91-10[1] | 6 | 5 | 7 | 4 |
| NEODOL 45-7[1] | 6 | 5 | 5 | 8 |
| NEODOL 23-2[1] | 3 | 5 | 3 | 3 |
| DEQUEST 2060[2] | 0.5 | 0.5 | 1.0 | 1.0 |
| Bleach Activator[3] | 6 | 6 | 4 | 7 |
| Citric Acid | 0.5 | 0.5 | 0.5 | 0.5 |
| NaOH | to pH 4 | to pH 4 | to pH 4 | to pH 4 |
| Hydrogen Peroxide | 7 | 3 | 2 | 7 |
| Water | Balance to 100% | Balance to 100% | Balance to 100% | Balance to 100% |

[1]Alkyl ethoxylate available from The Shell Oil Company.
[2]Commercially available from Monsanto Co.
[3]Bleach Activator according to any of Examples I–XXX.

| Ingredients | E wt % | F wt % | G wt % |
| --- | --- | --- | --- |
| Water | 73 | 75 | 71 |
| NEODOL 91-10[1] | 10 | 10 | 10 |
| NEODOL 23-2[1] | 5 | 5 | 5 |
| DEQUEST 2010[2] | 0.5 | 0.5 | 1.0 |
| Bleach Activator[3] | 4 | 4 | 8 |
| Citric Acid | 0.5 | 0.5 | 0.5 |
| NaOH | to pH 4 | to pH 4 | to pH 4 |
| Hydrogen Peroxide | 7 | 5 | 5 |

[1]Alkyl ethoxylate available from The Shell Oil Company.
[2]Commercially available from Monsanto Co.
[3]Bleach activator according to any of Examples I–XXX.

The bleaching solutions are prepared by a step of mixing any of the above compositions with water, typically yielding a concentration of the composition of about 1000 ppm. These bleaching solutions can be used in a subsequent step to launder fabrics under near neutral conditions in a U.S. domestic washing-machine, the pH of the wash water is typically in the range from about pH 6.5 to about 8.5, largely depending on the initial pH of the tap water. It is convenient for testing purposes to use a lightly soiled or clean bundle of consumer fabrics as test fabrics; additional test swatches of fabric comprising bleachable stains are typically added.

The laundering step typically involves washing fabrics at about 40° C., with excellent bleaching results, particularly with respect to bleaching as compared with otherwise identical compositions in which TAED, NOBS or benzoylcaprolactam are used at equal weight as a replacement for the performance-enhanced bleach activator. In particular, novel performance-enhanced bleach activators such as those of Examples III–XII provide superior results and are highly preferred.

Additional bleaching solutions are prepared by a step of mixing any of the above compositions in ADDITION to a bleach OR non-bleach detergent such as TIDE® with water. The additive composition is used at 1000 ppm, and the commercial detergent is used at 1000 ppm. These bleaching solutions can be used in a subsequent step to launder fabrics as described supra.

EXAMPLE XXXIII

This Example illustrates bleaching solutions which can be prepared by a step of mixing with water cleaning compositions having bleach additive form, more particularly, liquid bleach additive compositions without a hydrogen peroxide source, with an aqueous solution containing a hydrogen peroxide source, in accordance with the invention.

| Ingredients | A wt % | B wt % | C wt % | D wt % |
|---|---|---|---|---|
| NEODOL 91-10[1] | 6 | 5 | 7 | 10 |
| NEODOL 45-7[1] | 6 | 5 | 5 | 0 |
| NEODOL 23-2[1] | 3 | 5 | 3 | 5 |
| DEQUEST 2060[2] | 0.5 | 0.5 | 1.0 | 1.0 |
| Bleach Activator[3] | 6 | 6 | 4 | 7 |
| Citric Acid | 0.5 | 0.5 | 0.5 | 0.5 |
| NaOH | to pH 4 | to pH 4 | to pH 4 | to pH 4 |
| Water | Balance to 100% | Balance to 100% | Balance to 100% | Balance to 100% |

[1] Alkyl ethoxylate available from The Shell Oil Company.
[2] Commercially available from Monsanto Co.
[3] Bleach Activator according to any of Examples I–XXX.

These bleaching solutions can be used in a subsequent step to launder fabrics as described in example XXXII.

Additional bleaching solutions are prepared by a step of mixing any of the above compositions in ADDITION to a bleach detergent such as TIDE® WITH BLEACH in a wash test otherwise similar to that used in Example XXXII. The additive composition is used at 1000 ppm, and the commercial detergent is used at 1000 ppm. These bleaching solutions can be used in a subsequent step to launder fabrics as described in Example XXXII.

EXAMPLE XXXIV

This Example illustrates bleaching solutions which can be prepared by a step of mixing with water cleaning compositions having the form of granular laundry detergents as exemplified by the following formulations.

| INGREDIENT | A % | B % | C % | D % | E % |
|---|---|---|---|---|---|
| Bleach Activator* | 5 | 5 | 3 | 3 | 8 |
| Sodium Percarbonate | 0 | 5 | 15 | 0 | 0 |
| Sodium Perborate monohydrate | 5 | 0 | 0 | 10 | 20 |
| Brightener 49 | 0.4 | 0.4 | 0 | 0 | 0 |
| NaOH | 2 | 2 | 2 | 0 | 2 |
| Linear alkylbenzene-sulfonate, partially neutralized | 9 | 9 | 9 | 9 | 9 |
| Alkyl ethoxylate (C25E9) | 7 | 7 | 5 | 4 | 6 |
| Zeolite A | 32 | 20 | 7 | 17 | 21 |
| Acrylic Acid/Maleic Acid copolymer | 0 | 0 | 4 | 5 | 8 |
| Sodium polyacrylate | 0.6 | 0.6 | 0.6 | 0 | 0 |
| Diethylenetriamine penta(methylene phosphonic acid) | 0.5 | 0 | 0.5 | 0 | 1 |
| EDDS | 0 | 0.5 | 0 | 0.5 | 0 |
| Protease | 1 | 1 | 1.5 | 2.4 | 0.3 |
| Lipolase | 0 | 0 | 0 | 0.2 | 0 |
| Carezyme | 0 | 0 | 0 | 0.2 | 0 |
| Anionic soil release polymer | 0 | 0 | 0.5 | 0.4 | 0.5 |
| Dye transfer inhibiting polymer | 0 | 0 | 0.3 | 0.2 | 0 |
| Soda Ash | 22 | 22 | 22 | 22 | 22 |
| Silicate (2r) | 7.0 | 7.0 | 7.0 | 7.0 | 7.0 |
| Sulfate, Water, Perfume, Colorants | to 100 | to 100 | to 100 | to 100 | to 100 |

*Bleach activator according to any of Examples I–XXX

Any of the above bleaching solutions can be in a subsequent laundering step to launder fabrics under mildly alkaline conditions (pH 7–8). The pH can be adjusted by altering the proportion of acid to Na– salt form of alkylbenzenesulfonate. The laundering step typically involves washing fabrics at about 40° C., with excellent bleaching remits, particularly with respect to bleaching as compared with otherwise identical compositions in which TAED, NOBS or benzoylcaprolactam are used at equal weight as a replacement for the performance-enhanced bleach activator. In particular, novel performance-enhanced bleach activators, such as those of Examples III–XII, provide superior results and are highly preferred.

EXAMPLE XXXV

This Example illustrates bleaching solutions prepared by a step of mixing with water cleaning compositions having bleach additive form, more particularly, granular bleach additive compositions in accordance with the invention:

| Ingredient | % (wt.) |
|---|---|
| Bleach Activator* | 7.0 |
| Sodium Perborate (monohydrate) | 20.0 |
| Chelant (DTPA, acid form) | 10.0 |
| Citric Acid (coated) | 20.0 |
| Sodium Sulfate | Balance |

*Bleach Activator according to any of Examples I–XXX.

In an alternate embodiment, the composition is modified by replacing the sodium perborate with sodium percarbonate.

Any of the above bleaching solutions can be in a subsequent laundering step to launder fabrics as described in example XXXIV. Additional bleaching solutions are prepared by a step of mixing any of the above compositions in ADDITION to a bleach OR non-bleach detergent such as TIDE® with water. The additive composition is used at 1000 ppm, and the commercial detergent is used at 1000 ppm. These bleaching solutions can be used in a subsequent step to launder fabrics as described in example XXXII.

EXAMPLE XXXVI

This Example illustrates bleaching solutions prepared by a step of mixing with water cleaning compositions having liquid form especially useful for cleaning bathtubs and shower tiles without being harsh on the hands are as follows:

| Ingredient | % (wt.) A | % (wt.) B |
|---|---|---|
| Bleach Activator* | 7.0 | 5.0 |
| Hydrogen Peroxide | 10.0 | 10.0 |
| $C_{12}AS$, acid form, partially neutralized | 5.0 | 5.0 |
| $C_{12-14}AE_3S$, acid form, partially neutralized | 1.5 | 1.5 |
| $C_{12}$ DimethylAmine N-Oxide | 1.0 | 1.0 |
| DEQUEST 2060 | 0.5 | 0.5 |
| Sodium Citrate | 5.5 | 6.0 |
| Abrasive (15–25 micrometer) | 15.0 | 0 |
| HCL | to pH 4 | |
| Filler and water | Balance to 100% | |

*Bleach Activator according to any of Examples I–XXX.

EXAMPLE XXXVII

This Example illustrates bleaching solutions prepared by a step involving dissolution in water of cleaning compositions having a granular automatic dishwashing detergent composition as exemplified by the following.

| INGREDIENT | A wt % | B wt % | C wt % | D wt % |
|---|---|---|---|---|
| Bleach Activator (See Note 1) | 3 | 4.5 | 2.5 | 4.5 |
| Sodium Perborate Monohydrate (See Note 2) | 1.5 | 0 | 1.5 | 0 |
| Sodium Percarbonate (See Note 2) | 0 | 1.2 | 0 | 1.2 |
| Amylase (TERMAMYL ® from NOVO) | 1.5 | 2 | 2 | 2 |
| Dibenzoyl Peroxide | 0 | 0 | 0.8 | 0 |
| Transition Metal Bleach Catalyst (See Note 3) | 0 | 0.1 | 0.1 | 0 |
| Protease (SAVINASE ® 12 T, NOVO, 3.6% active protein) | 2.5 | 2.5 | 2.5 | 2.5 |
| Trisodium Citrate Dehydrate (anhydrous basis) | 7 | 15 | 15 | 15 |
| Citric Acid | 14 | 0 | 0 | 0 |
| Sodium Bicarbonate | 15 | 0 | 0 | 0 |
| Sodium Carbonate, anhydrous | 20 | 20 | 20 | 20 |
| BRITESIL H2O ®, PQ Corp. (as $SiO_2$) | 7 | 8 | 7 | 5 |
| Diethylenetriaminepenta-(methylenephosphonic acid), Na | 0 | 0 | 0 | 0.2 |
| Hydroxyethyldiphosphonate (HEDP), Sodium Salt | 0 | 0.5 | 0 | 0.5 |
| Ethylenediaminedisuccinate, Trisodium Salt | 0.1 | 0.3 | 0 | 0 |
| Dispersant Polymer (Accusol 480N) | 6 | 5 | 8 | 10 |
| Nonionic Surfactant (LF404, BASF) | 2.5 | 1.5 | 1.5 | 1.5 |
| Paraffin (Winog 70 ®) | 1 | 1 | 1 | 0 |
| Benzotriazole | 0.1 | 0.1 | 0.1 | 0 |
| Sodium Sulfate, water, minors BALANCE TO: | 100% | 100% | 100% | 100% |

Note 1: Bleach Activator according to any of Examples I–XXX.
Note 2: These hydrogen peroxide sources are expressed on a weight % available oxygen basis. To convert to a basis of percentage of the total composition, divide by about 0.15.
Note 3: Transition Metal Bleach Catalyst: MnEDDS according to U.S. Application Ser. No. 08/210,186, filed March 17, 1994.

EXAMPLE XXXVIII

A commercial rinse-aid block sold as "Jet-Dry" is modified as follows: The rinse aid block and about 5%–20% of a bleach activator according to any of Examples I–XXX are comelted, mixed and resolidified into block form. The resulting cleaning composition is used in an automatic dishwashing appliance with excellent spotting/filming and stain removal results.

EXAMPLE XXXIX

This Example illustrates bleaching solutions which can be prepared by a step of mixing with water cleaning compositions useful for cleaning typical householud surfaces. In the composition below, the hydrogen peroxide is separated as an aqueous solution from the other components by a suitable means such as a dual chamber container.

| Component | A (wt %) | B (wt %) |
|---|---|---|
| $C_{8-10}$ $E_6$ nonionic surfactant | 20 | 15 |
| $C_{12-13}E_3$ nonionic surfactant | 4 | 4 |
| $C_8$ alkyl sulfate anionic surfactant | 0 | 7 |
| $Na_2CO_3$/$NaHCO_3$ | 1 | 2 |
| $C_{12-18}$ Fatty Acid | 0.6 | 0.4 |
| Hydrogen peroxide | 7 | 7 |
| Bleach Activator* | 7 | 7 |
| Dequest 2060** | 0.05 | 0.05 |
| $H_2O$ | Balance to 100 | Balance to 100 |

*Bleach Activator according to any of Examples I–XXX.
**Commercially available from Monsanto Co.

What is claimed is:

1. A bleaching solution comprising:
   (a) an effective amount of a bleach activator having the formula RC(O)—L which produces a peracid RC(O)—OOH on perhydrolysis; wherein R is selected such that the difference in aqueous $pK_a$ between acetic acid and the carboxylic ring analog, RC(O)OH, of said peracid is at least 0.6 and L is a leaving group; said bleach activator having a perhydrolysis selectivity coefficient, $Kp/K_D$ of at least about 5 and a low-pH perhydrolysis-efficiency coefficient of at least about 0.15; and
   (b) an effective amount of an oxygen bleach source; said bleaching solution having low soil resistivity.

2. A bleaching solution according to claim 1 which is substantially free from organic dry-cleaning solvents and wherein said bleach activator upon perhydrolysis forms at most one mole equivalent of a peracid per mole of bleach activator.

3. A bleaching solution according to claim 2 formed by adding a bleach additive composition comprising said bleach activator to an aqueous alkaline cleaning bath comprising said oxygen bleach source.

4. A bleaching solution according to claim 2 in which said low pH perhydrolysis efficiency coefficient is least about 0.30.

5. A bleaching solution according to claim 2 in which said oxygen bleach source is selected from the group consisting of hydrogen peroxide, perborate salts, percarbonate salts, peroxymonosulfate salts, and peroxydisulfate salts.

6. A bleaching solution according to claim 2 in which said oxygen bleach source is selected from the group consisting of perborate salts, percarbonate salts and mixtures thereof and wherein said bleach activator is selected from the group consisting of:

p-nitrobenzoyl caprolactam; p-nitrobenzoylvalerolactam; linear or branched C2–C9 alkylsulfonylbenzoylcaprolactam;

linear or branched C2–C9 alkylsulfonyl-benzoyl-valerolactam;

linear or branched C2–C9 alkyloxysulfonylbenzoylcaprolactam;

linear or branched C2–C9 alkyloxysulfonylbenzoylvalerolactam;

linear or branched C2–C9 alkyl(amino)sulfonylbenzoylcaprolactam;

linear or branched C2–C9 alkyl(amino)sulfonylbenzoylvalerolactam;

linear or branched C2–C9 alkylsulfonylnaphthylcaprolactam; linear or branched C2–C9 alkylsulfonylnaphthylvalerolactam; linear or branched C2–C9 alkyloxysulfonylnaphthylcaprolactam; linear or branched C2–C9 alkyloxysulfonylnaphthylvalerolactam; linear or branched C2–C9 alkyl(amino)sulfonylnaphthylcaprolactam; linear or branched C2–C9 alkyl(amino)sulfonylnaphthylvalerolactam;

2-furoylcaprolactam; 2-furoylvalerolactam; 3-furoylcaprolactam; 3-furoylvalerolactam; 5-nitro-2-furoylcaprolactam; 5-nitro-2-furoylvalerolactam; 1-naphthylcaprolactam; 1-naphthylvalerolactam; and mixtures thereof.

7. A bleaching solution according to claim 6 in which the initial level of said oxygen bleach source in said bleaching solution upon formation is from about $10^{-4}$ to about $10^{-10}$ moles per mole of said bleach activator.

8. A bleaching solution according to claim 6 wherein the pH of said bleaching solution, as formed, is from about 6.5 to about 9.5.

9. A bleaching solution according to claim 8 in which the pH of said bleaching solution, as formed, is from about 7 to about 9.

10. A bleaching solution according to claim 9 wherein said activator is at an initial level of from about 1 to about 300 ppm of said bleaching solution.

11. A bleaching solution according to claim 10 wherein said bleaching solution has a low soil level resistivity.

12. A bleaching solution according to claim 11 which is substantially free from phosphate builders.

13. A bleaching solution according to claim 12 which is substantially free from chlorine bleach.

14. A bleaching solution according to claim 1 wherein R is a chloro, bromo, or nitro substituted phenyl moiety and L is valerolactam.

15. A method for forming a bleaching solution comprising the step of reacting under aqueous conditions, effective amounts of
   (a) a bleach activator having the formula RC(O)—L which produces a peracid RC(O)—OOH on perhydrolysis; wherein R is selected such that the difference in aqueous PKa between acetic acid and the carboxylic ring analog, RC(O)OH, of said peracid is at least 0.6 and L is a leaving group; said bleach activator having a perhydrolysis selectivity coefficient, $K_P/K_D$ of at least about 5 and a low-pH perhydrolysis-efficiency coefficient of at least-about 0.15 ; and
   (b) an effective amount of an oxygen bleach source.

16. A method according to claim 15 wherein said bleach activator forms at most one mole equivalent of a peracid per mole of bleach activator when perhydrolyzed.

17. A method according to claim 15 further comprising a preceding step of adding a bleach additive composition comprising said bleach activator to an aqueous alkaline cleaning bath comprising said oxygen bleach source in dissolved form.

18. A method for bleaching fabrics comprising a method according to claim 15 followed by a step comprising treating fabrics with said bleaching solution.

19. A method according to claim 15 wherein said step is a supplementary step in an otherwise conventional method for washing dishware in a domestic automatic dishwashing appliance.

20. A method according to claim 19 in which said step is further characterized in that it a post-mainwash step in which said oxygen bleach source consists essentially of rinse-cycle carryover.

21. A method according to claim 15 further comprising a preceding step of dissolving a granular or tablet-form detergent comprising both said bleach activator and said oxygen bleach source.

22. A method according to claim 15 in which said low pH perhydrolysis efficiency coefficient is least about 0.30.

23. A method according to claim 15 in which said oxygen bleach source is selected from the group consisting of hydrogen peroxide, perborate salts, percarbonate salts, peroxymonosulfate salts, and peroxydisulfate salts.

24. A method according to claim 15 in which said bleach activator has an aqueous solubility at 25° C. of about 100 ppm or higher.

25. A method according to claim 15 in which said oxygen bleach source is selected from the group consisting of perborate salts, percarbonate salts and mixtures thereof and wherein said bleach activator is selected from the group consisting of:

p-nitrobenzoyl caprolactam; p-nitrobenzoylvalerolactam; linear or branched C2–C9 alkylsulfonylbenzoylcaprolactam; linear or branched C2–C9 alkylsulfonylbenzoylvalerolactam; linear or branched C2–C9 alkyloxysulfonylbenzoylcaprolactam; linear or branched C2–C9 alkyloxysulfonyl-benzoylvalerolactam; linear or branched C2–C9 alkyl(amino)sulfonylbenzoylcaprolactam; linear or branched C2–C9 alkyl(amino)-sulfonylbenzoylvalerolactam; linear or branched C2–C9 alkylsulfonylnaphthylcaprolactam; linear or branched C2–C9 alkylsulfonylnaphthylvalerolactam; linear or branched C2–C9 alkyloxysulfonylnaphthylcaprolactam; linear or branched C2–C9 alkyloxysulfonylnaphthylvalerolactam; linear or branched C2–C9 alkyl(amino)sulfonylnaphthylcaprolactam; linear or branched C2–C9 alkyl(amino)sulfonylnaphthylval-erolactam; 2-furoylcaprolactam; 2-furoylvalerolactam; 3-furoylcaprolactam; 3-furoylvalerolactam; 5-nitro-2-furoylcaprolactam; 5-nitro-2-furoylvalerolactam; 1-naphthylcaprolactam; 1-naphthylvalerolactam; and mixtures thereof.

26. A method according to claim 25 in which the initial level of said oxygen bleach source in said bleaching solution upon formation is from about $10^{-4}$ to about $10^{-10}$ moles per mole of said bleach activator.

27. A method according to claim 26 wherein the pH of said bleaching solution, as formed, is from about 7 to about 8.5.

28. A method according to claim 27 wherein said activator is at an initial level of from about 1 to about 300 ppm of said bleaching solution.

* * * * *